United States Patent
Salentine et al.

(10) Patent No.: US 10,314,798 B2
(45) Date of Patent: Jun. 11, 2019

(54) COMPOSITIONS AND METHODS FOR TREATING ALZHEIMER'S DISEASE AND PARKINSON'S DISEASE

(71) Applicant: Biotie Therapies, Inc., South San Francisco, CA (US)

(72) Inventors: Christopher G. Salentine, San Rafael, CA (US); Thomas R. Malefyt, Carmel Valley, CA (US)

(73) Assignee: Biotie Therapies, Inc., South San Francisco, CA (US)

( * ) Notice: Subject to any disclaimer, the term of this patent is extended or adjusted under 35 U.S.C. 154(b) by 0 days.

(21) Appl. No.: 15/720,947

(22) Filed: Sep. 29, 2017

(65) Prior Publication Data

US 2018/0092868 A1 Apr. 5, 2018

Related U.S. Application Data

(60) Provisional application No. 62/402,357, filed on Sep. 30, 2016.

(51) Int. Cl.
*A61K 31/17* (2006.01)
*A61K 9/20* (2006.01)

(52) U.S. Cl.
CPC ............ *A61K 31/17* (2013.01); *A61K 9/2054* (2013.01); *A61K 9/2077* (2013.01)

(58) Field of Classification Search
CPC ..... A61K 31/17; A61K 9/2054; A61K 9/2077
See application file for complete search history.

(56) References Cited

U.S. PATENT DOCUMENTS

| 7,312,359 | B2 | 12/2007 | Greenhouse et al. |
| 7,713,954 | B2 | 5/2010 | Bonhaus et al. |
| 8,093,424 | B2 | 1/2012 | Greenhouse et al. |
| 8,269,040 | B2 * | 9/2012 | Jerussi ................ A61K 9/2054 562/590 |
| 8,889,906 | B2 | 11/2014 | Greenhouse et al. |
| 2005/0142193 | A1 | 6/2005 | Tang et al. |
| 2008/0095845 | A1 | 4/2008 | Luber et al. |
| 2014/0323628 | A1 * | 10/2014 | Jeol .......................... C08K 5/17 524/249 |
| 2014/0348932 | A1 | 11/2014 | Yang et al. |
| 2015/0266817 | A1 | 9/2015 | Greenhouse et al. |

FOREIGN PATENT DOCUMENTS

| WO | WO-2006066790 A1 * | 6/2006 | .......... C07C 317/32 |
| WO | WO 2018/064559 A1 | 4/2018 | |

OTHER PUBLICATIONS

International Search Report and Written Opinion for International Patent Application No. PCT/US2017/054473, dated Dec. 15, 2017, 11 pages.
Wicke, et al., "Investigational drugs targeting 5-HT6 receptors for the treatment of Alzheimer's disease." Expert Opinion on Investigational Drugs (2015); 24(12): 1515-1528.

* cited by examiner

*Primary Examiner* — Sarah Pihonak
(74) *Attorney, Agent, or Firm* — Cooley LLP

(57) ABSTRACT

The present invention is directed to tablets for oral administration to a subject, comprising a therapeutically effective amount of SYN120 or a pharmaceutically acceptable salt thereof, wherein the tablet is substantially free of lactose. The present invention is also directed to methods for treating diseases or conditions including Alzheimer's disease and/or Parkinson's disease, comprising administering to a patient in need thereof tablets regarding the same.

23 Claims, 7 Drawing Sheets

Fig. 1 Elution Chromatogram of SYN120 and Impurity
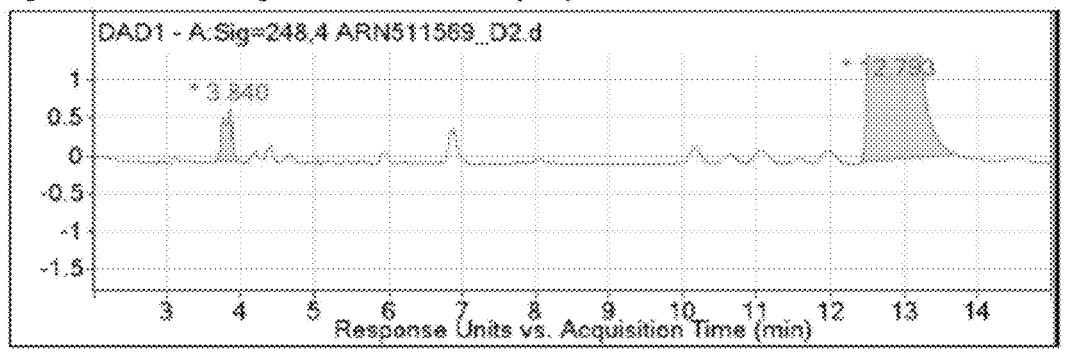
Fig. 2 Mass Spectrum and Elemental Formula of the Impurity
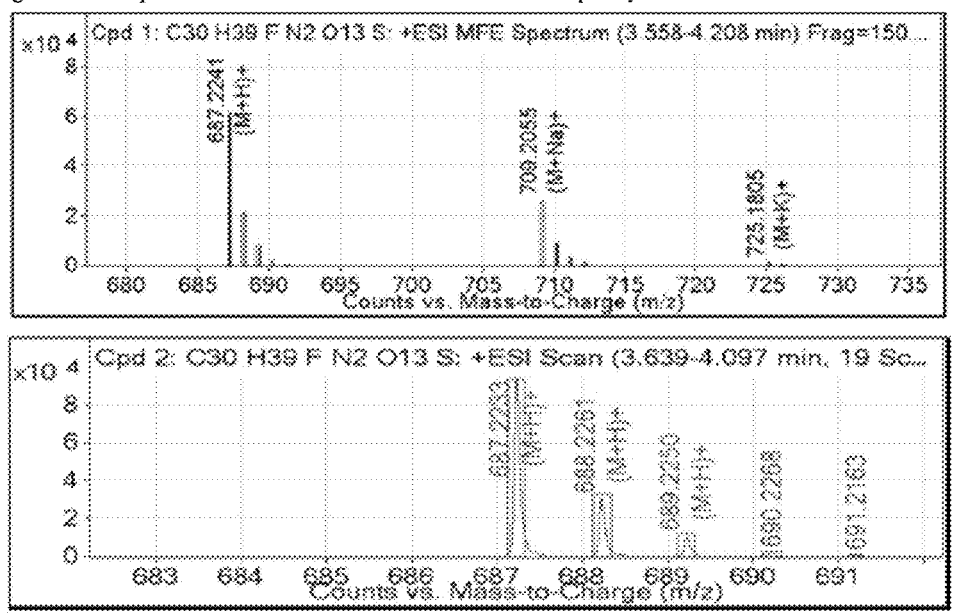

Fig 3: MS/MS Spectra of Impurity at RRT 0.30 (top) and SYN20 (bottom)
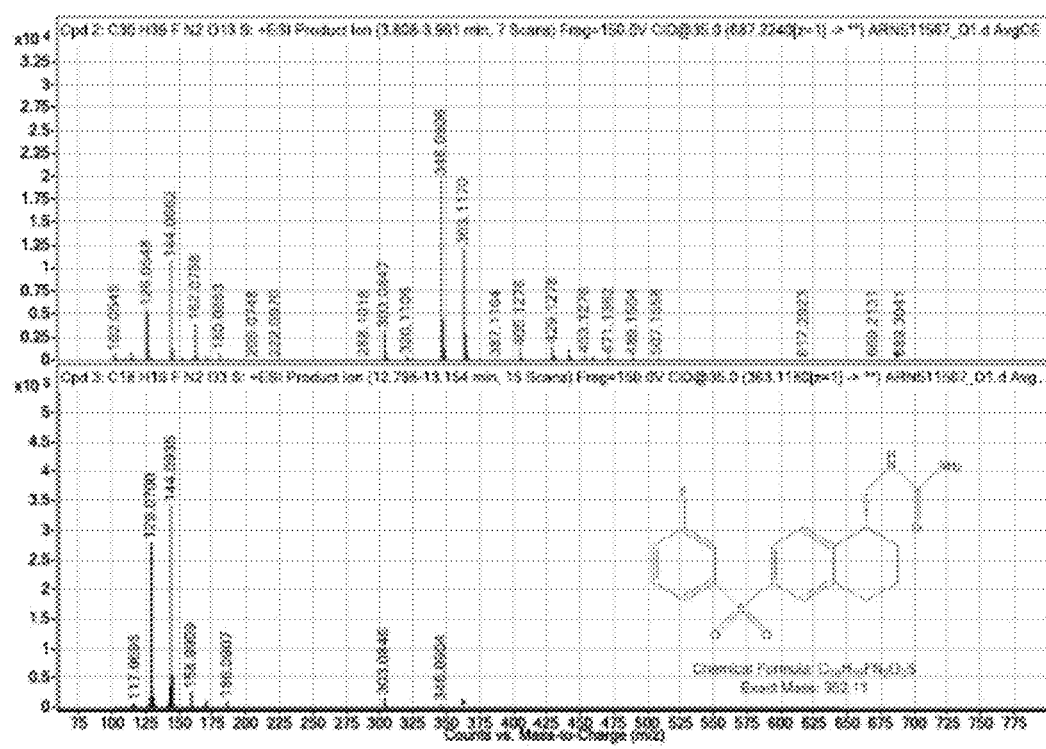

Fig. 4: Proposed Mechanism of Lactose Reacting with SYN120 to form Impurity
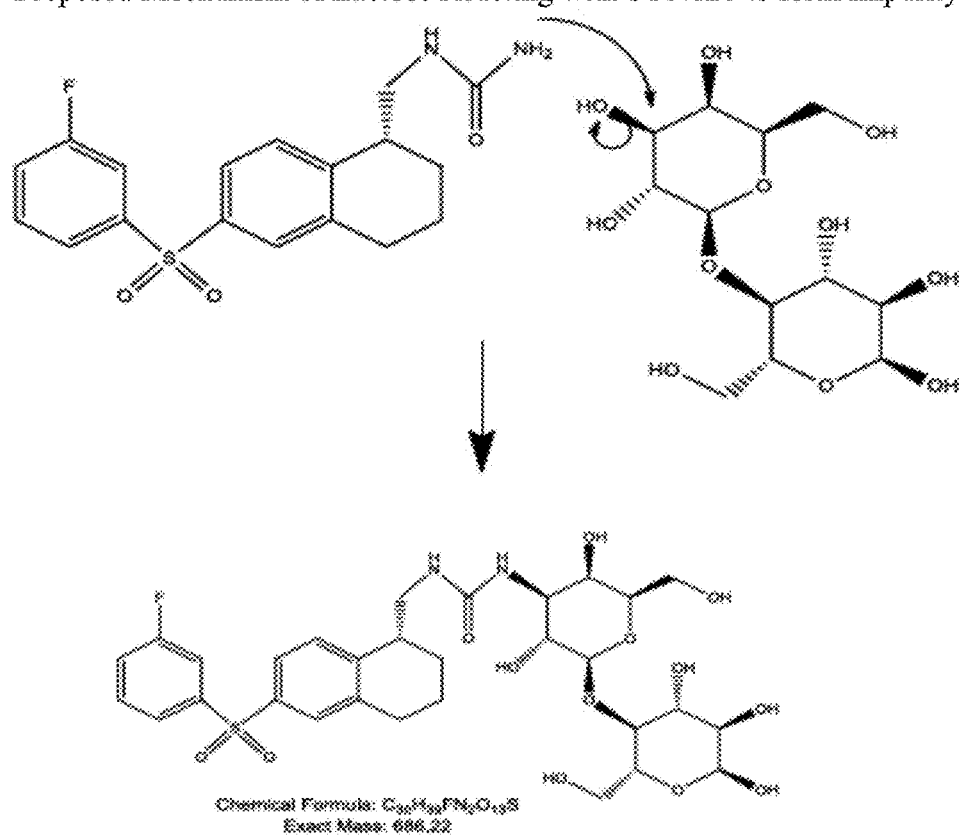

Fig. 5: SYN120 granules manufacturing process
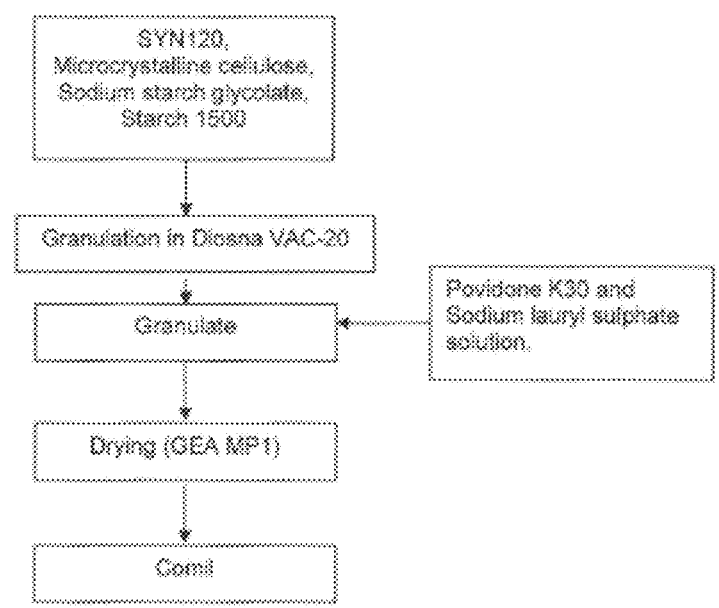

Fig. 6 A-B: Mean plasma SYN120 concentrations following 2 mg to 600 mg SYN120 as a single oral dose
6A. Linear Scale
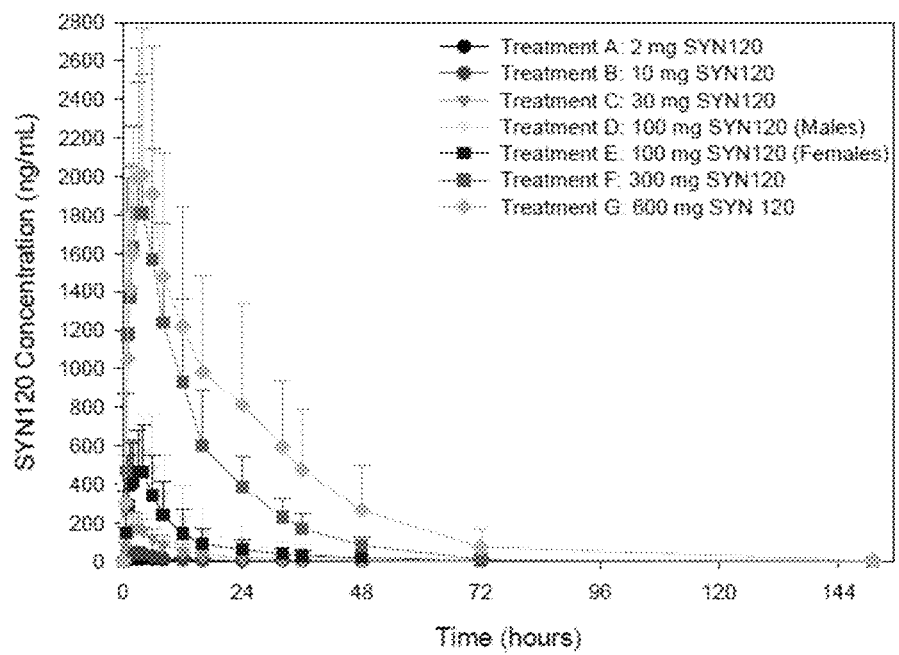
6B. Semi-log Scale
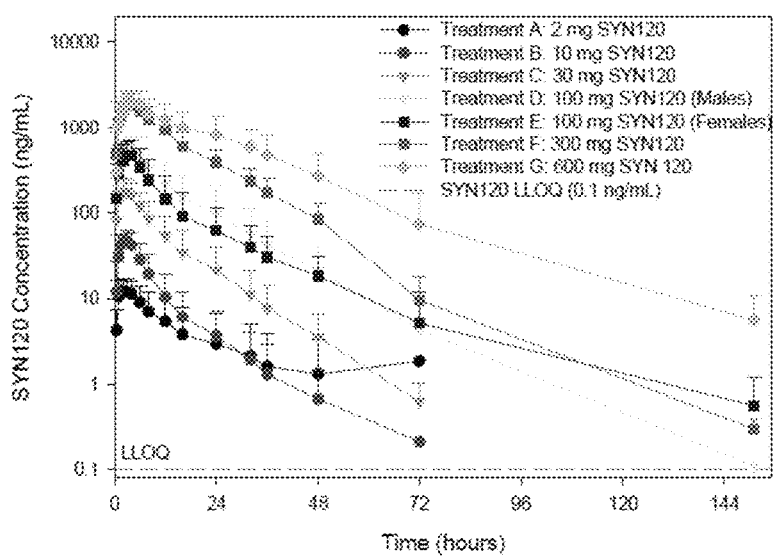

Fig. 7A-B: Mean Plasma Concentrations of SYN120 on Day 1 Following dose of 100 mg, 300 mg, 600 mg SYN120
7A: Linear Scale
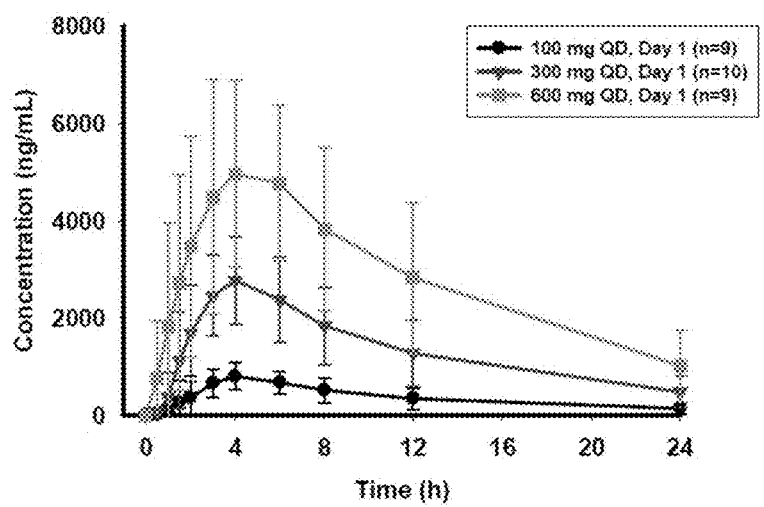
7B: Semi-log Scale
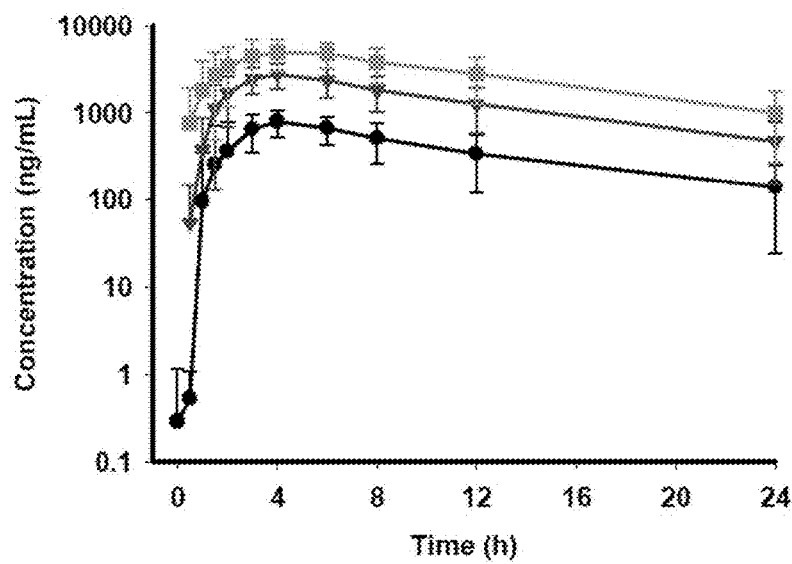

Fig. 8A-B: : Mean Plasma Concentrations of SYN120 on Day 14 following once daily dose of 100 mg, 300 mg, 600 mg SYN120
8A: Linear Scale
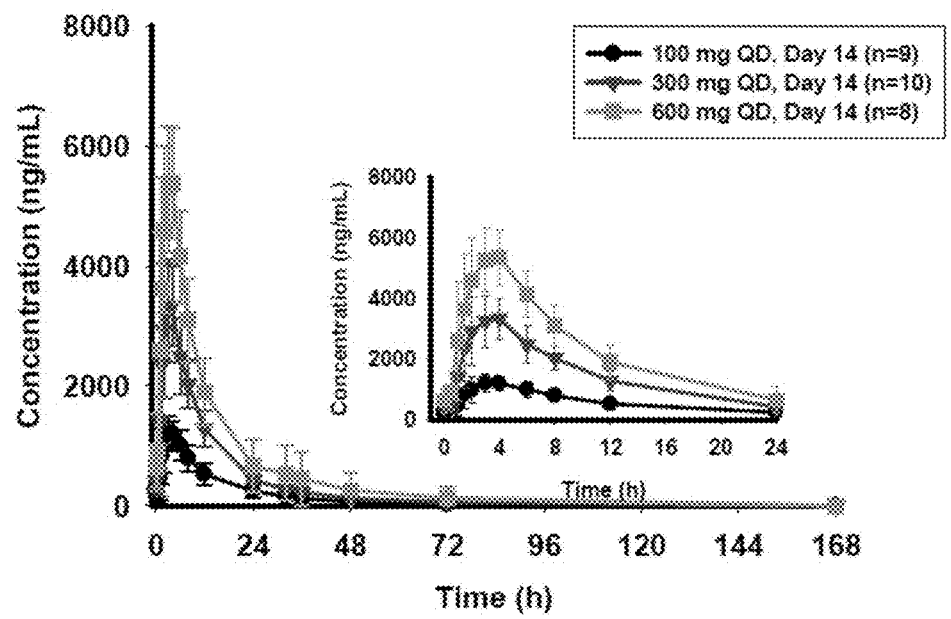
8B: Semi-log Scale
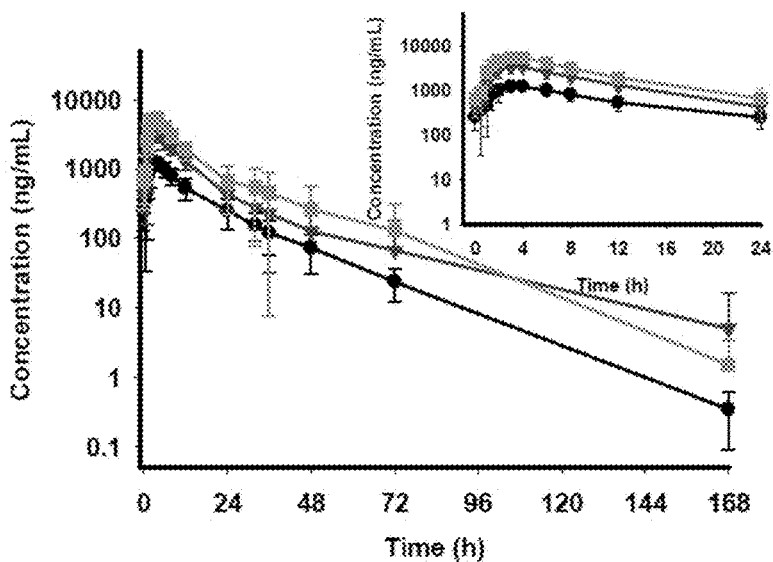

COMPOSITIONS AND METHODS FOR TREATING ALZHEIMER'S DISEASE AND PARKINSON'S DISEASE

CROSS-REFERENCE TO RELATED PATENT APPLICATIONS

The present application claims priority to, and the benefit of U.S. Provisional Patent Application Ser. No. 62/402,357, filed Sep. 30, 2016, which is hereby incorporated by reference in its entirety for all purposes.

BACKGROUND OF THE INVENTION

Alzheimer's disease is the most common form of dementia occurring primarily in the elderly. It is a progressive neurodegenerative disease that affects over 3.1 million people in the US and 26.6 million people worldwide. Given the general aging of the population, the overall prevalence of Alzheimer's disease is expected to increase in the coming years. Researchers predict that global prevalence of Alzheimer's disease will quadruple by 2050 to more than 100 million.

Although not considered one of the core features of Alzheimer's disease and other dementias, neuropsychiatric symptoms are being increasingly recognized as important factors influencing the quality of life for patients and caregivers and may be the trigger for nursing home placement.

Most current treatments aimed at improving the cognitive dysfunction are based on the hypothesis that the cognitive deficits of Alzheimer's disease can be traced to loss of function in the cholinergic system in the CNS. Acetylcholinesterase inhibitors represent the mainstay of current Alzheimer's disease therapy, including donepezil (Aricept®), galantamine (Reminyl®), and rivastigmine (Exelon®). While these cholinergic-enhancing treatments produce some symptomatic improvement in some patients, therapeutic response has not been satisfactory for the majority of patients treated.

Dementia greatly affects quality of life for both patients and caregivers with Parkinson's disease as well. Safe and effective treatment options for dementia are much needed. Current treatments for Parkinson's disease dementia are mostly derived from those utilized in Alzheimer's disease. Rivastigmine, the only FDA-approved medication for Parkinson's disease dementia, is the first line treatment. However, more effective treatments are needed to help patients suffering from cognitive dysfunction. There thus remains a high unmet medical need for the treatment of neuropsychiatric symptoms, particularly of psychotic symptoms, and adverse cognitive effects due to Alzheimer's disease and/or Parkinson's disease.

SUMMARY OF THE INVENTION

One embodiment of the present invention includes compositions comprising SYN120. In another embodiment, the compositions of the present invention may be a tablet. In another embodiment, the tablet may be for oral administration to a subject. In another embodiment, the tablets for oral administration may include a therapeutically effective amount of SYN120 or a pharmaceutically acceptable salt thereof. In another embodiment, the composition/tablet of the present invention may also include microcrystalline cellulose. In another embodiment, the composition/tablet of the present invention is substantially free of lactose. In still another embodiment, the composition/tablet of the present invention is substantially free of mannitol. In yet another embodiment, the composition/tablet of the present invention is substantially free of both lactose and mannitol.

In another embodiment, the tablet comprises about 2.5 mg to about 200 mg of SYN120 or a pharmaceutically acceptable salt thereof. In another embodiment, the tablet comprises about 50 mg to about 100 mg of SYN120 or a pharmaceutically acceptable salt thereof. In another embodiment, the tablet comprises about 5 mg to about 15 mg of SYN120 or a pharmaceutically acceptable salt thereof.

In another embodiment, the tablet may include about 5 mg, 10 mg, 50 mg or 100 mg of SYN120 or a pharmaceutically acceptable salt thereof. In another embodiment, the tablet may include about 5 mg of SYN120 or a pharmaceutically acceptable salt thereof. In another embodiment, the tablet may include about 10 mg of SYN120 or a pharmaceutically acceptable salt thereof. In another embodiment, the tablet may include about 20 mg of SYN120 or a pharmaceutically acceptable salt thereof. In another embodiment, the tablet may include about 25 mg of SYN120 or a pharmaceutically acceptable salt thereof. In another embodiment, the tablet may include about 30 mg of SYN120 or a pharmaceutically acceptable salt thereof. In another embodiment, the tablet may include about 45 mg of SYN120 or a pharmaceutically acceptable salt thereof. In another embodiment, the tablet may include about 50 mg of SYN120 or a pharmaceutically acceptable salt thereof. In another embodiment, the tablet may include about 60 mg of SYN120 or a pharmaceutically acceptable salt thereof. In another embodiment, the tablet may include about 75 mg of SYN120 or a pharmaceutically acceptable salt thereof. In another embodiment, the tablet may include about 100 mg of SYN120 or a pharmaceutically acceptable salt thereof. In another embodiment, the tablet may include about 125 mg of SYN120. In another embodiment, the tablet may include about 150 mg of SYN120 or a pharmaceutically acceptable salt thereof. In another embodiment, the tablet may include about 175 mg of SYN120 or a pharmaceutically acceptable salt thereof. In another embodiment, the tablet may include about 200 mg of SYN120 or a pharmaceutically acceptable salt thereof.

Suitable daily doses of the SYN120 tablets of the present invention may range from about 20 mg/day to about 100 mg/day, for example as a single daily dose, or alternatively in multiple daily doses (2 or more). In a particular embodiment, the daily dose is 20 mg/day, 50 mg/day, 100 mg/day, or 200 mg/day. In another embodiment, the daily dose of SYN120 is 20 mg/day or a pharmaceutically acceptable salt thereof. In another embodiment, the daily dose of SYN120 is 25 mg/day or a pharmaceutically acceptable salt thereof. In another embodiment, the daily dose of SYN120 is 30 mg/day or a pharmaceutically acceptable salt thereof. In another embodiment, the daily dose of SYN120 is 40 mg/day or a pharmaceutically acceptable salt thereof. In another embodiment, the daily dose of SYN120 is 50 mg/day or a pharmaceutically acceptable salt thereof. In another embodiment, the daily dose of SYN120 is 60 mg/day or a pharmaceutically acceptable salt thereof. In another embodiment, the daily dose of SYN120 is 70 mg/day or a pharmaceutically acceptable salt thereof. In another embodiment, the daily dose of SYN120 is 80 mg/day or a pharmaceutically acceptable salt thereof. In another embodiment, the daily dose of SYN120 is 90 mg/day or a pharmaceutically acceptable salt thereof. In another embodiment, the daily dose of SYN120 is 100 mg/day or a pharmaceutically acceptable salt thereof. In another embodiment, the daily dose of SYN120 is 110 mg/day. In another embodiment, the daily dose of SYN120 is 120 mg/day. In another embodiment, the daily dose of SYN120 is 130 mg/day. In another embodiment, the daily dose of SYN120 is 140 mg/day. In another embodiment, the daily dose of SYN120 is 150 mg/day. In another embodiment, the daily dose of SYN120 is 160 mg/day. In another embodiment, the daily dose of SYN120 is 170 mg/day. In another embodiment, the daily dose of SYN120 is 180 mg/day. In another embodiment, the daily dose of SYN120 is 190 mg/day. In another embodiment, the daily dose of SYN120 is 200 mg/day. In some cases, or for some patients, higher daily doses of the tablets can be administered, for example 300 mg/day or 600 mg/day. In another embodiment, the daily dose of SYN120 is 300 mg/day. In another embodiment, the daily dose of SYN120 is 325 mg/day. In another embodiment, the daily dose of SYN120 is 350 mg/day. In another embodiment, the daily dose of SYN120 is 375 mg/day. In another embodiment, the daily dose of SYN120 is 400 mg/day. In another embodiment, the daily dose of SYN120 is 425 mg/day. In another embodiment, the daily dose of SYN120 is 450 mg/day. In another embodiment, the daily dose of SYN120 is 475 mg/day. In another embodiment, the daily dose of SYN120 is 500 mg/day. In another embodiment, the daily dose of SYN120 is 525 mg/day. In another embodiment, the daily dose of SYN120 is 550 mg/day. In another embodiment, the daily dose of SYN120 is 575 mg/day. In another embodiment, the daily dose of SYN120 is 600 mg/day. A typical maximum daily dose is 600 mg/day, and a typical minimum daily dose is 10 mg/day.

In another embodiment of the present invention, the tablet is an immediate release tablet. In another embodiment, at least 90% of SYN120 or a pharmaceutically acceptable salt thereof is released in 60 minutes when tested for dissolution using a USP II paddle apparatus at a speed of 75 rpm in 900 mL of 0.2% w/v Sodium Lauryl Sulfate (SLS) in pH 1.2 Hydrochloric Acid (37% v/v) at 37° C.

In another embodiment, at least 80% of SYN120 or a pharmaceutically acceptable salt thereof is released in 30 minutes when tested for dissolution using a USP II paddle apparatus at a speed of 75 rpm in 900 mL of 0.2% w/v Sodium Lauryl Sulfate (SLS) in pH 1.2 Hydrochloric Acid (37% v/v) at 37° C.

In another embodiment, at least 70% of SYN120 or a pharmaceutically acceptable salt thereof is released in 15 minutes when tested for dissolution using a USP II paddle apparatus at a speed of 75 rpm in 900 mL of 0.2% w/v Sodium Lauryl Sulfate (SLS) in pH 1.2 Hydrochloric Acid (37% v/v) at 37° C.

In another embodiment, the composition/tablet of the present invention may include microcrystalline cellulose. In a specific embodiment, the microcrystalline cellulose is selected from one or more partially depolymerized alpha-celluloses, typically having a particle size in the range of about 50 μm to about 180 μm, for example Avicel PH-101 and Avicel PH-102 (partially depolymerized alpha-cellulose made by hydrolysis of wood pulp, available from FMC Biopolymer; 50 μm particle size and 100 μm particle size, respectively, and 3.0-5.0% moisture).

In another embodiment, the tablet is substantially free of mannitol. In another embodiment, the tablet has a mean tablet hardness of about 4 kP to about 15 kP (for example, about 5 kP).

The present invention also includes methods of treating Alzheimer's disease and/or Parkinson's disease, comprising administering to a patient in need thereof the SYN120 compositions/tablets of the present invention.

In a specific embodiment, the present invention includes methods of treating Alzheimer's disease comprising administering to a patient in need thereof the SYN120 compositions/tablets of the present invention. In another specific embodiment, the present invention includes methods of treating Parkinson's disease comprising administering to a patient in need thereof the SYN120 compositions/tablets of the present invention.

The present invention further includes methods of initiating treatment with the SYN120 compositions or tablets of the present invention, comprising titrating the dose of SYN120 from an initial daily dose of about 20 mg/day for about 1 week, then about 50 mg/day for about 1 week, then about 100 mg/day thereafter. In other embodiments, the present invention includes methods of initiating treatment with the SYN120 compositions or tablets of the present invention, comprising titrating the dose of SYN120 from an initial daily dose of about 50 mg/day for about 1 week, then about 100 mg/day thereafter. In still other embodiments, the present invention includes methods of initiating treatment with the SYN120 compositions or tablets of the present invention, comprising titrating the dose of SYN120 from an initial daily dose of about 50 mg/day for about 1 week, then about 100 mg/day for about 1 week, then 200 mg/day thereafter.

The present invention also includes methods of improving cognitive function of a patient, comprising administering to a patient in need thereof the SYN120 compositions/tablets of the present invention. In another embodiment, the patient has been diagnosed with Alzheimer's disease. In another embodiment, the patient has been diagnosed with Parkinson's disease.

BRIEF DESCRIPTION OF THE DRAWINGS

FIG. 1 shows the Elution Chromatogram of SYN120 and Impurity from a SYN120 Tablet using lactose as a diluent.

FIG. 2 shows the Mass Spectrum and Elemental Formula of the Impurity.

FIG. 3 shows the MS/MS Spectra of Impurity at RRT 0.30 (top) and SYN120 (bottom).

FIG. 4 shows the proposed mechanism of lactose covalently reacting with SYN120 to form the impurity.

FIG. 5 shows a diagram of the scaled-up SYN120 granule manufacturing process

FIGS. 6A-6B show the mean plasma concentrations following 2 mg to 600 mg SYN120 after oral administration as a single dose. FIG. 6A shows linear scale and FIG. 6B shows semi-log scale.

FIGS. 7A-7B show the mean plasma concentrations of SYN120 on day 1 following the oral administration of 100 mg, 300 mg or 600 mg SYN120. FIG. 7A shows a linear scale and FIG. 7B shows a semi-log scale.

FIGS. 8A-8B show the mean plasma concentrations of SYN120 on day 14 following the orally administered once-daily dose of 100 mg, 300 mg or 600 mg SYN120. FIG. 8A shows a linear scale and FIG. 8B shows a semi-log scale.

DETAILED DESCRIPTION OF THE INVENTION

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

The term "pharmaceutically acceptable" means biologically or pharmacologically compatible for in-vivo use in animals or humans, and can mean approved by a regulatory agency of the Federal or a state government or listed in the U.S. Pharmacopeia or other generally recognized pharmacopeia for use in animals, and more particularly in humans.

The term "substantially free of" as used herein, means free from therapeutically effective amounts of compounds when administered in suggested doses, but may include trace amounts of compounds in non-therapeutically effective amounts. With respect to compositions of the present invention which are "substantially free of" reducing sugars such as lactose, and/or sugar alcohols such as mannitol, de minimis amounts of such reducing sugars like lactose, and/or mannitol can be present, for example, less than about 10%, less than about 9%, less than about 8%, less than 7%, less than 6%, less than about 5%, less than about 4%, less than about 3%, less than about 2%, less than about 1%, less than about 0.5%, inclusive of all ranges and subranges therebetween.

The term "subject," as used herein, comprises any and all organisms and includes the term "patient." "Subject" may refer to a human or any other animal.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

The term "administrable" defines a composition that is able to be given to a patient. Likewise, "administering" refers to the act of giving a composition to a patient or otherwise making such composition available to a patient or the patient taking a composition.

As used herein, the term "about," when located before a dosage amount or dosage range of a specific ingredient, refers to an amount or range closely above and/or closely below the stated amount or range that does not manifestly alter the therapeutic effect of the specific ingredient from the stated amount or range.

As used herein, the term "immediate release" (IR) refers to release of greater than or equal to about 80% of the drug within about one hour following administration of the dosage form. Alternatively, the term "immediate release" (IR) refers to release of greater than or equal to about 80% of the drug in 60 minutes when tested for dissolution using a USP II paddle apparatus at a speed of 75 rpm in 900 mL of 0.2% w/v Sodium Lauryl Sulfate (SLS) in pH 1.2 Hydrochloric Acid (37% v/v) at 37° C.

For the purpose of this application, "lactose" will be used to refer to any of the various common forms of lactose, such as anhydrous α-lactose, anhydrous β-lactose, amorphous lactose, and lactose monohydrate.

Similarly, for the purpose of this application, "mannitol" will be used to refer to any of the various common forms of mannitol, such as the known α-, β-, and δ-mannitol polymorphs, amorphous forms, hydrates, hemihydrates, etc.

The present invention relates to compositions comprising the compound SYN120. SYN120 has the structure as identified below.

SYN120 Structure

SYN120 is a potent, high-affinity ($pK_i$ 9.6) antagonist of the 5-$HT_6$ receptor. 5-$HT_6$ receptors are expressed almost exclusively in the brain, where they activate gamma-aminobutyric acid (GABA) neurotransmission. Antagonists of these receptors increase the release of glutamate and acetylcholine. This dual enhancement of glutamatergic and cholinergic neurotransmission is believed to contribute to procognitive effects of 5-$HT_6$ antagonists as observed in rodents and primates. Clinical data also suggest that 5-$HT_6$ antagonists may attenuate age and scopolamine-induced cognitive deficits in humans.

SYN120 is also known to bind to and act as an antagonist to the 5-$HT2_A$, 5-$HT2_B$, and 5-$HT2_C$ receptors ($pK_i$ 7.8, 7.7, and 8.1, respectively). Like other subtypes, the 5-HT2 receptors bind serotonin (5-hydroxytryptamine, 5-HT). The receptors are G protein-coupled receptors and mediate neurotransmission. Modulation of the 5-HT2 receptor subtypes, particularly the 5-HT2a subtype, has been shown in animals and humans to have procognitive effects and also improve other neurological abnormalities such as neuropsychiatric disturbances. It is thus predicted that SYN120, through its multiple modes of action, will improve neurologic deficiencies in humans, including impaired cognition like memory, attention, learning, and decision making, as well as neuropsychiatric disturbances such as hallucinations, delusions, confusion, agitation, sleep disorders, anxiety, and depression. As such, it is predicted to be a useful treatment for cognitive and psychiatric disorders due to neurodegeneration such as Alzheimer's disease, Parkinson's disease, and Huntington's disease, as well as other forms of dementia (e.g. Lewy Body Dementia, frontotemporal dementia, Down's Syndrome, autism, cognitive impairment associated with schizophrenia, and multiple sclerosis), anxiety, depression, manic depression, psychoses, epilepsy, autism, obsessive compulsive disorders, mood disorders, migraine, sleep disorders, eating disorders such as anorexia, bulimia and obesity, panic attacks, akathisia, attention deficit hyperactivity disorder, attention deficit disorder, withdrawal from drug abuse (e.g., from cocaine, ethanol, nicotine and benzodiazepines), schizophrenia and neurological disorders associated with spinal trauma, head injury, or stroke and cerebral vascular disease. SYN120 can also be useful for treating GI disorders such as functional bowel disorder.

The SYN120 compound is described in U.S. Pat. Nos. 7,312,359; 8,093,424; 8,889,906; and 7,713,954, each of which is incorporated by reference herein in their entirety. Although the SYN120 compound was screened for the treatment of cognitive disorders in these patents, they only provide general disclosures regarding SYN120 in various dosage forms such as oral tablets. Specifically, neither these patents nor the prior art describe any specific compositions, suggest any compatibility issues of SYN120 when combined with common pharmaceutically acceptable excipients known in the art, or provide any guidance as to dosing or desirable pharmacokinetic (PK) suitable for treating the conditions described herein. Rather, they suggest that SYN120 can be formulated with conventional carriers such as magnesium carbonate, magnesium stearate, talc, sugar, lactose, pectin, dextrin, starch, gelatin, tragacanth, methylcellulose, sodium carboxymethylcellulose, a low 50 melting wax, cocoa butter, and the like.

However, the present inventors have found that SYN120 unexpectedly and covalently reacts with a very commonly used diluent, lactose, thereby producing an undesirable impurity and unstable pharmaceutical composition with the drug. Indeed, lactose is the most common and prevalent diluent in the pharmaceutical industry for used in oral immediate release tablets. Examples 1 and 2 below provide manufactured oral tablets with 100 mg SYN120 and 5 mg SYN120 respectively. Stability studies of the tablets in Examples 1 and 2, however, showed an unknown impurity in the tablet. It was determined that this impurity was not the active drug SYN120, nor any of the excipients in the tablet. See FIGS. 1-4.

The present invention thus in certain embodiments relates to formulations and pharmaceutical compositions that include a therapeutically effective amount of SYN120 or a pharmaceutically acceptable salt thereof. In a specific embodiment, due to the unexpected covalent reaction of SYN120 with lactose, the formulations and pharmaceutical compositions of the present invention may be substantially free of lactose. Furthermore, the covalent reaction between SYN120 and reducing sugars such as lactose is particularly unexpected due to the low nucleophilicity and basicity of the "amine" portion of the urea group in SYN120. See FIGS. 1-4. As seen in FIG. 4, it is believed that the amine portion of the urea group acts as a nucleophile, reacting by a mechanism similar to a Maillard-type reaction wherein the result is a glycosidic bond of the amine to lactose. Such a reaction is certainly unexpected in view of the low nucleophilicity of the SYN120 amine due to electron pair delocalization from the amide linkage, particularly compared to a much stronger nucleophilic primary amine (or secondary amine) that is more commonly known to react with lactose in a Maillard-type reaction.

Furthermore, it is known that the Maillard-type reaction of more nucleophilic primary amines (or secondary amines) commonly occurs with lactose because it is a reducing sugar, i.e., a sugar that has a free aldehyde group or free ketone group. Although the amino of SYN120 unexpectedly reacts with lactose due the low nucleophilicity, a similar reaction can occur with SYN120 and other reducing sugars. Accordingly, in one embodiment, the formulations and pharmaceutical compositions are substantially free of a reducing sugar. In another embodiment, the formulations and pharmaceutical compositions are substantially free of a reducing sugar selected from the group consisting of lactose, galactose, glucose, maltose, fructose, ribose and/or xylose. In another embodiment, the formulations and pharmaceutical compositions are also substantially free of any isomer or pharmaceutically acceptable derivative of a reducing sugar. For example, the formulations and pharmaceutical compositions of the present invention may also be substantially free of any reducing sugar isomer or pharmaceutically acceptable derivative of lactose and/or mannitol. In a specific embodiment, compositions of the present invention are substantially free of isomers of lactose, such as sucrose, trehalose, maltose, isomaltose, maltulose, isomaltulose, turanose, and cellobiose. In another embodiment, are substantially free of isomers of mannitol, such as sorbitol, and compounds closely related to mannitol, such as xylitol, erythritol, lactitol, and maltitol.

In a specific embodiment, the compositions of the present invention are in the form a solid dosage form or composition, such as a pill, capsule, tablet, gel caplet, softgel, lozenge, wafers etc. In a specific embodiment, the solid dosage form is a tablet. In another specific embodiment, the tablet is for oral administration to a subject.

In another embodiment, the present inventions may include methods for administering the tablets or SYN120 compositions of the present invention to a subject. In another embodiment, the methods may include administering the tablets or SYN120 compositions to a subject to treat negative effects of Alzheimer's disease and/or Parkinson's disease.

In a specific embodiment, the present invention includes methods of treating Alzheimer's disease comprising administering to a patient in need thereof the SYN120 compositions/tablets of the present invention. In another specific embodiment, the present invention includes methods of treating Parkinson's disease comprising administering to a patient in need thereof the SYN120 compositions/tablets of the present invention.

Due to the incompatibility of SYN120 combined with lactose, SYN120 tablet formulations with other diluents were studied. For example, other diluents such as mannitol and microcrystalline cellulose were studied for both stability and adequate hardness and friability. See Examples 4-6. It was unexpectedly discovered, however, that mannitol also has compatibility problems in the SYN120 tablets. For example, Table 6 indicates that SYN120 5 mg tablets fail to compress, showing a low mean tablet hardness (1.48 kP) which would fail friability requirements for commercial distribution. Accordingly, in another embodiment of the present invention, the tablet is substantially free of the diluent mannitol.

Examples 5-7 show manufactured tablets comprising microcrystalline cellulose. Stability studies and compression studies indicate that SYN120 tablets at 5 mg 50 mg and 100 mg dosage amounts are stable in a tablet formulation. Accordingly, in another embodiment of the present invention, the SYN120 tablets of the present invention may include the diluent microcrystalline cellulose. In another embodiment, the microcrystalline cellulose is selected from one or more of the group consisting of Avicel PH-101 and Avicel PH-102.

In another embodiment, suitable diluents may include e.g. calcium carbonate, dibasic calcium phosphate, tribasic calcium phosphate, calcium sulfate, microcrystalline cellulose, powdered cellulose, dextrans, dextrin, dextrose, fructose, kaolin, sorbitol, starch, pregelatinized starch, sucrose, sugar etc. In a specific embodiment, the diluent is substantially free of both lactose and mannitol.

In another embodiment, the tablets of the present invention may include starch and microcrystalline cellulose as the diluents. In another embodiment, the starch is starch 1500, a grade of pregelatinized starch.

Other pharmaceutically acceptable excipients such as fillers, glidants, disintegrants, binders, lubricants, coating agents, etc., may be added to the present invention. Other pharmaceutically acceptable excipients include acidifying agents, alkalizing agents, preservatives, antioxidants, buffering agents, chelating agents, coloring agents, complexing agents, emulsifying and/or solubilizing agents, surfactants, flavors and perfumes, humectants, sweetening agents, wetting agents etc., may be added to the present invention.

Examples of suitable fillers, diluents and/or binders include microcrystalline cellulose (various grades of Avicel®, Ceolus®, Elcema®, Vivacel®, Ming Tai or Solka-Floc®), hydroxypropylcellulose, L-hydroxypropylcellulose (low substituted), low molecular weight hydroxypropyl methylcellulose (HPMC) (e.g. Methocel E, F and K from Dow Chemical, Metolose SH from Shin-Etsu, Ltd), hydroxyethylcellulose, sodium carboxymethylcellulose, carboxymethylhydroxyethyl cellulose and other cellulose derivatives, agarose, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, collagen etc.

Examples of suitable disintegrants include e.g. alginic acid or alginates, microcrystalline cellulose, hydroxypropyl cellulose and other cellulose derivatives, croscarmellose sodium, crospovidone, polacrillin potassium, sodium starch glycolate, starch, pregelatinized starch, carboxymethyl starch (e.g. Primogel® and Explotab®) etc.

Specific examples of glidants and lubricants include stearic acid, magnesium stearate, calcium stearate or other metallic stearates, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate etc.

In certain embodiments, disintegrating agents (e.g., cross-linked polyvinyl pyrrolidone, agar, sodium starch glycolate or alginic acid or a salt thereof, such as sodium alginate) are added.

In another embodiment, the compositions of the present invention may include different dosage amounts of SYN120. In a specific embodiment, the compositions present invention may include about 2.5 mg to about 200 mg of SYN120. In another embodiment, the compositions may include about 50 mg to about 100 mg of SYN120. In another embodiment, the compositions may include about 5 mg to about 15 mg of SYN120. In another embodiment, the compositions may include about 5 mg, 10 mg, 50 mg or 100 mg of SYN120. In another embodiment, the compositions of the various SYN120 ranges and dosage amounts may be in the form of a tablet.

In another embodiment, the compositions may include about 5 mg of SYN120. In another embodiment, the compositions may include about 10 mg of SYN120. In another embodiment, the compositions may include about 20 mg of SYN120. In another embodiment, the compositions may include about 25 mg of SYN120. In another embodiment, the compositions may include about 30 mg of SYN120. In another embodiment, the compositions may include about 45 mg of SYN120. In another embodiment, the compositions may include about 50 mg of SYN120. In another embodiment, the compositions may include about 60 mg of SYN120. In another embodiment, the compositions may include about 75 mg of SYN120. In another embodiment, the compositions may include about 100 mg of SYN120. In another embodiment, the compositions may include about 125 mg of SYN120. In another embodiment, the compositions may include about 150 mg of SYN120. In another embodiment, the compositions may include about 175 mg of SYN120. In another embodiment, the compositions may include about 200 mg of SYN120.

In another embodiment, the compositions of the present invention may include different low dosage amounts of SYN120. In a specific embodiment, the compositions present invention may include about 0.1 mg to about 5 mg of SYN120. In another embodiment, the compositions may include about 0.5 mg to about 2.5 mg of SYN120. In another embodiment, the compositions may include about 1 mg of SYN120. In another embodiment, the compositions may include about 2 mg of SYN120. In another embodiment, the compositions may include about 3 mg of SYN120. In another embodiment, the compositions may include about 4 mg of SYN120. In another embodiment, the compositions may include about 5 mg of SYN120.

Suitable daily doses of the SYN120 compositions of the present invention range from about 20 mg/day to about 100 mg/day, for example as a single daily dose, or alternatively in multiple daily doses (2 or more). In a particular embodiment, the daily dose is 20 mg/day, 50 mg/day, 100 mg/day, or 200 mg/day. In some cases, or for some patients, higher daily doses can be administered, for example 300 mg/day or 600 mg/day A typical maximum daily dose is 600 mg/day, and a typical minimum daily dose is 10 mg/day.

In another embodiment, the daily dose of SYN120 is 20 mg/day. In another embodiment, the daily dose of SYN120 is 25 mg/day. In another embodiment, the daily dose of SYN120 is 30 mg/day. In another embodiment, the daily dose of SYN120 is 40 mg/day. In another embodiment, the daily dose of SYN120 is 50 mg/day. In another embodiment, the daily dose of SYN120 is 60 mg/day. In another embodiment, the daily dose of SYN120 is 70 mg/day. In another embodiment, the daily dose of SYN120 is 80 mg/day. In another embodiment, the daily dose of SYN120 is 90 mg/day. In another embodiment, the daily dose of SYN120 is 100 mg/day. In another embodiment, the daily dose of SYN120 is 110 mg/day. In another embodiment, the daily dose of SYN120 is 120 mg/day. In another embodiment, the daily dose of SYN120 is 130 mg/day. In another embodiment, the daily dose of SYN120 is 140 mg/day. In another embodiment, the daily dose of SYN120 is 150 mg/day. In another embodiment, the daily dose of SYN120 is 160 mg/day. In another embodiment, the daily dose of SYN120 is 170 mg/day. In another embodiment, the daily dose of SYN120 is 180 mg/day. In another embodiment, the daily dose of SYN120 is 190 mg/day. In another embodiment, the daily dose of SYN120 is 200 mg/day.

In another embodiment, the daily dose of SYN120 is 300 mg/day. In another embodiment, the daily dose of SYN120 is 325 mg/day. In another embodiment, the daily dose of SYN120 is 350 mg/day. In another embodiment, the daily dose of SYN120 is 375 mg/day. In another embodiment, the daily dose of SYN120 is 400 mg/day. In another embodiment, the daily dose of SYN120 is 425 mg/day. In another embodiment, the daily dose of SYN120 is 450 mg/day. In another embodiment, the daily dose of SYN120 is 475 mg/day. In another embodiment, the daily dose of SYN120 is 500 mg/day. In another embodiment, the daily dose of SYN120 is 525 mg/day. In another embodiment, the daily dose of SYN120 is 550 mg/day. In another embodiment, the daily dose of SYN120 is 575 mg/day. In another embodiment, the daily dose of SYN120 is 600 mg/day.

In another embodiment, the SYN120 compositions of the present invention may be initiated in the form of an ascending dosing protocol. In another embodiment, the ascending dosing protocol can be initiated at a same daily dose for a certain amount of time, such as for one day, two days, three days, four days, five days, six days, seven days, 1 week, 2 weeks, 3 weeks or 4 weeks. The daily dose can then be increased for a certain amount of time, such as using the increased daily dose for one day, two days, three days, four days, five days, six days, seven days, 1 week, 2 weeks, 3 weeks or 4 weeks. In yet, another embodiment, the daily dose can then be increased again for a certain amount of time, such as for one day, two days, three days, four days, five days, six days, seven days, 1 week, 2 weeks, 3 weeks or 4 weeks. In a specific embodiment, the SYN120 compositions may be in a specific dosage form, such as a tablet.

In another embodiment, the ascending dosing protocol, as described directly above, may be within a range of daily dosages. In one embodiment, the initial daily dose of SYN120 may be about 10 mg/day to about 300 mg/day. In another embodiment, the initial daily dose of SYN120 is 20 mg/day. In another embodiment, the initial daily dose of SYN120 is 25 mg/day. In another embodiment, the initial daily dose of SYN120 is 30 mg/day. In another embodiment, the initial daily dose of SYN120 is 40 mg/day. In another embodiment, the initial daily dose of SYN120 is 50 mg/day. In another embodiment, the initial daily dose of SYN120 is 60 mg/day. In another embodiment, the initial daily dose of SYN120 is 70 mg/day. In another embodiment, the initial daily dose of SYN120 is 80 mg/day. In another embodiment, the initial daily dose of SYN120 is 90 mg/day. In another embodiment, the initial daily dose of SYN120 is 100 mg/day. In another embodiment, the initial daily dose of SYN120 is 110 mg/day. In another embodiment, the initial daily dose of SYN120 is 120 mg/day. In another embodiment, the initial daily dose of SYN120 is 130 mg/day. In another embodiment, the initial daily dose of SYN120 is 140 mg/day. In another embodiment, the initial daily dose of SYN120 is 150 mg/day. In another embodiment, the initial daily dose of SYN120 is 160 mg/day. In another embodiment, the initial daily dose of SYN120 is 170 mg/day. In another embodiment, the initial daily dose of SYN120 is 180 mg/day. In another embodiment, the initial daily dose of SYN120 is 190 mg/day. In another embodiment, the initial daily dose of SYN120 is 200 mg/day.

In another embodiment, the increased daily dose of SYN120 may be from a range of about about 20 mg/day to about 600 mg/day. In another embodiment, the increased daily dose of SYN120 is 20 mg/day. In another embodiment, the increased daily dose of SYN120 is 50 mg/day. In another embodiment, the increase daily dose of SYN120 is 100 mg/day. In another embodiment, the increased daily dose of SYN120 is 150 mg/day. In another embodiment, the increased daily dose of SYN120 is 200 mg/day. In another embodiment, the increased daily dose of SYN120 is 250 mg/day. In another embodiment, the increase daily dose of SYN120 is 300 mg/day. In another embodiment, the increased daily dose of SYN120 is 350 mg/day. In another embodiment, the increased daily dose of SYN120 is 400 mg/day. In another embodiment, the increased daily dose of SYN120 is 450 mg/day. In another embodiment, the increased daily dose of SYN120 is 500 mg/day. In another embodiment, the increased daily dose of SYN120 is 550 mg/day. In another embodiment, the increased daily dose of SYN120 is 600 mg/day.

In another embodiment, there may be another increased daily dose of SYN120 in the ascending dosing regimen, wherein the daily dose may range from about 25 mg/day to about 600 mg/day. In another embodiment, the increased daily dose of SYN120 is 20 mg/day. In another embodiment, the increased daily dose of SYN120 is 50 mg/day. In another embodiment, the increase daily dose of SYN120 is 100 mg/day. In another embodiment, the increased daily dose of SYN120 is 150 mg/day. In another embodiment, the increased daily dose of SYN120 is 200 mg/day. In another embodiment, the increased daily dose of SYN120 is 250 mg/day. In another embodiment, the increase daily dose of SYN120 is 300 mg/day. In another embodiment, the increased daily dose of SYN120 is 350 mg/day. In another embodiment, the increased daily dose of SYN120 is 400 mg/day. In another embodiment, the increased daily dose of SYN120 is 450 mg/day. In another embodiment, the increased daily dose of SYN120 is 500 mg/day. In another embodiment, the increased daily dose of SYN120 is 550 mg/day. In another embodiment, the increased daily dose of SYN120 is 600 mg/day.

In some embodiments, dosing of the SYN120 compositions of the present invention are initiated in the form of an ascending dosing protocol, wherein dosing is initiated at a low dose, e.g., about 20 or 50 mg/day, then gradually increased over time, to about 50 or 100 mg/day, and if needed further increased to about 200 mg/day until a suitable maintenance dose is achieved. For example, dosing can be initiated at 20 mg/day for 1 or 2 weeks, then increased to 50 mg/day for 1 or 2 weeks, before increasing to a maintenance dose of 100 mg/day. For some patients, dosing can be initiated at about 50 mg/day for 1 or 2 weeks, then increased to 100 mg/day thereafter, or optionally for 1 or 2 weeks before increasing the dose yet again to about 200 mg/day. Such ascending dose protocols reduce the incidence of adverse events during maintenance treatment with SYN120.

In some embodiments, dosing may be initiated in the form of an ascending dosing protocol that is not specific to a particular composition of the invention. In one embodiment, the dosing may be initiated at a low dose and gradually increased over time. Regardless of the composition, the initial dose may be about 20 or 50 mg/day, then gradually increased over time, to about 50 or 100 mg/day, and if needed further increased to about 200 mg/day until a suitable maintenance dose is achieved. For example, dosing can be initiated at 20 mg/day for 1 or 2 weeks, then increased to 50 mg/day for 1 or 2 weeks, before increasing to a maintenance dose of 100 mg/day. For some patients, dosing can be initiated at about 50 mg/day for 1 or 2 weeks, then increased to 100 mg/day thereafter, or optionally for 1 or 2 weeks before increasing the dose yet again to about 200 mg/day.

In another embodiment, the dosing may be initiated at a low dose and gradually increased over time wherein the initial dose, increased dose, dosing regimen is dependent on a particular composition of the invention as disclosed herein. The initial dose may be about 20 or 50 mg/day, then gradually increased over time, to about 50 or 100 mg/day, and if needed further increased to about 200 mg/day until a suitable maintenance dose is achieved. For example, dosing can be initiated at 20 mg/day for 1 or 2 weeks, then increased to 50 mg/day for 1 or 2 weeks, before increasing to a maintenance dose of 100 mg/day. For some patients, dosing can be initiated at about 50 mg/day for 1 or 2 weeks, then increased to 100 mg/day thereafter, or optionally for 1 or 2 weeks before increasing the dose yet again to about 200 mg/day.

In another embodiment, the tablet is in the form of an immediate release tablet. In another embodiment, at least 90% of SYN120 is released in 60 minutes when tested for dissolution. In another embodiment, at least 80% of SYN120 is released in 30 minutes when tested for dissolution. In another embodiment, at least 70% of SYN120 is released in 15 minutes when tested for dissolution. In another embodiment, the dissolution is tested using USP II paddle apparatus at a speed of 75 rpm in 900 mL of 0.2% w/v Sodium Lauryl Sulfate (SLS) in pH 1.2 Hydrochloric Acid (37% v/v) at 37° C.

In another embodiment, about 80% to about 95% (for example about 90%) of SYN120 is released in 60 minutes when tested for dissolution. In another embodiment, about 60% to about 85% of SYN120 is released in 30 minutes when tested for dissolution. In another embodiment, about 50% to about 75% of SYN120 is released in 15 minutes when tested for dissolution. In another embodiment, the dissolution is tested using USP II paddle apparatus at a speed of 75 rpm in 900 mL of 0.2% w/v Sodium Lauryl Sulfate (SLS) in pH 1.2 Hydrochloric Acid (37% v/v) at 37° C.

The compositions/tablets of the present invention are formulated to provide (after a single dose) about 85% to about 120% of a geometric mean $C_{max}$ of about 12 ng/mL (2 mg dose), about 50 ng/mL (10 mg dose), about 180 ng/mL (30 mg dose), about 500 to about 600 ng/mL (100 mg dose), about 1700 ng/mL (300 mg dose), about 2100 ng/mL (600 mg dose). The compositions/tablets of the present invention are formulated to provide (after a single dose) about 85% to about 120% of a geometric mean $AUC_{0-24}$ of about 120 ng·hr/mL (2 mg dose), about 350 ng·hr/mL (10 mg dose), about 1550 ng·hr/mL (30 mg dose), about 4000 to about 5900 ng·hr/mL (100 mg dose), about 21300 ng·hr/mL (300 mg dose), or about 27600 ng·hr/mL (600 mg dose). The compositions/tablets of the present invention are formulated to provide (after a single dose) about 85% to about 120% of a geometric mean $AUC_{0-\infty}$ of about 150 ng·hr/mL (2 mg dose), about 390 ng·hr/mL (10 mg dose), about 1760 ng·hr/mL (30 mg dose), about 5000 to about 7100 ng·hr/mL (100 mg dose), about 27400 ng·hr/mL (300 mg dose), or about 43000 ng·hr/mL (600 mg dose). The compositions/tablets of the present invention provide a median $T_{max}$ ranging from about 1 hour to about 6 hours, including about 1 hour, about 2 hours, about 3 hours, about 4 hours, about 5 hours, or about 6 hours, inclusive of all ranges and subranges therein.

SYN120 has an elimination half-life ($t_{1/2}$) ranging from about 8 to about 12 hours. After repeated dosing with 100 mg SYN120 (e.g., one or more weeks after the 100 mg/day maintenance dose of SYN120 is reached), patients typically have plasma levels of SYN120 ranging from about 300 ng/mL to about 1200 ng/mL. When the compositions of the present invention are dosed once per day (typically in the morning), plasma levels of SYN120 after maintenance dosing will fluctuate within a defined range, typically peaking within 1-4 hours after administration. The plasma levels during the maintenance dosing period can be characterized by the "steady-state" plasma concentration, $C_{SS}$, i.e., the average plasma concentration measured over the dosing period. In order to minimize adverse events, the compositions of the present invention provide a $C_{SS}$ value upon QD dosing of 100 mg SYN120 ranging from about 300 ng/mL to about 1200 ng/mL. Alternatively, or in addition, the compositions of the present invention are administered so as to provide a ratio of the maximum plasma concentration ($C_{max}$) to the minimum plasma concentration ($C_{min}$) which is no more than about 10. Alternatively the ratio of $C_{max}/C_{min}$ is no more than about 9, about 8, about 7, about 6, about 5, about 4, about 3, or about 2.

In another embodiment, the tablets of the present invention have acceptable hardness and friability for a pharmaceutical composition. Tablet formulations need to meet acceptable tablet hardness and friability, which is required for e.g., bulk packaging and/or packaging in HDPE bottles or push-through blisters (most preferred packaging), for transportation, commercial distribution, and/or end use.

In another embodiment, the tablets may have sufficient mean hardness at the appropriate compaction force. In another embodiment, the tablets of the present invention have a mean tablet hardness of about 4.0 kP to about 15 kP. In another embodiment, the tablets of the present invention have a mean tablet hardness of about 5.0 kP to about 12 kP. In another embodiment, the tablets of the present invention have a mean tablet hardness of about 6.0 kP to about 10 kP.

Having now generally described the invention, the same will be more readily understood through reference to the following examples, which are provided by way of illustration and are not intended to be limiting of the present invention.

EXAMPLES

Example 1: Tablet Formulation with Lactose

Table 1 below shows the formulation composition of SYN120 100 mg uncoated tablets with 60% w/w drug loading

TABLE 1

Tablet Formulation of SYN120 100 mg tablets (lactose)

| Ingredient | % w/w | mg/tablet | grams/batch |
|---|---|---|---|
| SYN120 | 60 | 100 | 240 |
| Lactose (350M) | 3.6 | 6 | 14.4 |
| Starch 1500 | 25 | 41.67 | 100 |
| Sodium starch glycolate | 5 | 8.33 | 20 |
| Povidone K30 | 5 | 8.33 | 20 |
| Sodium lauryl sulfate | 0.4 | 0.67 | 1.6 |
| Magnesium Stearate | 1 | 1.67 | 4 |
| TOTAL | 100 | 166.67 | 400 |

Initially the required quantity of povidone K-30 and sodium lauryl sulfate were dissolved in 75 g of water and stirred for 60 minutes. SYN120, lactose monohydrate, starch 1500, sodium starch glycolate were screened through a 600 micron mesh and transferred to the Diosna P1-6 high shear granulator equipped with a 1 L bowl. The contents of the granulator were then dry mixed. After dry mixing, the contents were granulated according to the following parameters:

| | |
|---|---|
| Impeller speed (rpm) | 700-800 |
| Chopper speed (rpm) | 1500 |
| Current (amp) | 3.0 |
| Product temperature (deg C.) | 34.2 |
| Binder addition rate (grams/min) | 20 |
| Duration (mins) | 9.0 |

After wet massing, the granules were transferred into the GEA Strea 1 fluid bed drier.

The granules were dried for 45 minutes at 50° C. The granules were then blended with magnesium stearate in a 2 L IBC for 2 minutes at 25 rpm. No processing issues were incurred during the granulation process. The granules were then compressed into tablets using the IMA Kilian Pressima 8 station tablets compression machine.

Example 2: Tablet Formulation with Lactose

Table 2 below shows the formulation composition of SYN120 5 mg uncoated tablets with 3% w/w drug loading. The SYN120 60% w/w granules were diluted with extra-granular excipients to yield a final compression blend for the 5 mg tablets.

TABLE 2

Formulation composition of SYN120 5 mg Tablets (lactose)

| Ingredient | % w/w | mg/tablet | grams/batch |
|---|---|---|---|
| INTRA-GRANULAR | | | |
| SYN120 | 3.0 | 5 | 24 |
| Lactose (Pharmatose 350M) | 0.18 | 0.3 | 1.44 |
| Starch 1500 | 1.25 | 2.08 | 10 |
| Sodium starch glycolate | 0.25 | 0.42 | 2 |
| Povidone K30 | 0.25 | 0.42 | 2 |
| Sodium lauryl sulfate | 0.02 | 0.03 | 0.16 |
| EXTRA-GRANULAR | | | |
| Lactose (Super Tab 11SD) | 79 | 131.67 | 632 |
| Starch 1500 | 10 | 16.67 | 80 |
| Sodium starch glycolate | 5 | 8.33 | 40 |
| Magnesium stearate | 1.05 | 1.75 | 8.4 |
| TOTAL | 100 | 166.67 | 800 |

The required quantity of granules and 250.66 grams of lactose (Super Tab 11SD) were transferred to a 2 L IBC. The contents were then blended for 5 minutes at 25 rpm and then unloaded and passed through a U3 Comil at 2200 rpm equipped with a 910 micron screen. The comilled granules/lactose were transferred to the 2 L IBC and a further 250.66 grams of lactose (Super Tab 11SD) was added; the contents were blended for 10 minutes at 25 rpm.

A further 130.68 grams of lactose (Super Tab 11 SD) and the required quantity of starch 1500 and sodium starch glycolate were added; the contents were blended for 10 minutes at 25 rpm. The required quantity of magnesium stearate was passed through a 425 micron screen and added to the blend. The blend was then lubricated for 2 minutes at 25 rpm. The blend was compressed using the IMA Kilian Pressima equipped with 7 mm round debossed tooling (only 4 stations tooled)

Example 3: Stability Tests of Tablet Formulations with Lactose

After compression of the SYN120 tablet formulations comprising lactose, samples of tablets taken from long-term and accelerated stability studies were analyzed using LC-MS analysis. Specifically, 5 tablets from each sample were dissolved in an appropriate diluent and diluted to obtain a final concentration of about 0.05-0.1 mg/mL of SYN120. An aliquot of each sample was centrifuged for about 10 minutes at 3500 rpm, followed by a further 5 mins at 4000 rpm until a clear supernatant was achieved. The supernatant was then sampled for analysis.

Initial LC-MS analysis identified an unknown impurity, wherein the SYN120 eluted and had a peak at about 12.8 minutes for each of three sample preparations, wherein the impurity of interest had a peak and eluted at 3.8 minutes (RRT 0.30). (See FIG. 1). Mass Spectrum and an elemental formula of the Impurity eluted at 3.8 minutes (RRT 0.30) is provided in FIG. 2. The molecular feature extraction algorithm software on MassHunter predicted an elemental formula for the impurity. Due, however, to the large molecular weight of the impurity and thus the difficulty in determining the structure, fragmentation analysis was performed on both the SYN120 elution and impurity elution.

The fragmentation profile of both the SYN120 and the impurity resulted in several identical peaks in their respective mass spectra, indicating that the impurity was related to the SYN120 (See FIG. 3). The fragments impurity included m/z 303.08 (C17H16FO2S), m/z 346.09 (C18H17FO3S) and probably most significantly at m/z 363.12, the mass of the SYN120 itself. The accurate mass elemental compositions of all these fragments corresponded with viable fragments within the SYN120 structure. Based on this evidence, it was apparent that the SYN120 was reacting with another compound to form the impurity.

The excipient materials within the formulation had their masses determined, and it emerged that a potential Maillard-type condensation reaction between the amino group on the SYN120 structure and a hydroxyl group on lactose would result in an impurity with the correct mass (The elemental formula of this theoretical structure matched the mass, isotope spacing and isotopic distribution of the impurity by accurate mass analysis as featured in the red boxes in FIG. 2).

A nucleophilic substitution mechanism for the genesis of the impurity is provided in FIG. 4, and the MS/MS fragmentation profile of the impurity can be compared with the structure. The fragments generated match the proposed structure, including a sequential loss of hydroxyl groups from the lactose region of the compound between m/z 180.09 and m/z 108.04, characterized by a mass difference of 18 amu between neighboring peaks.

Evidence obtained during the analysis of the impurity—including the mass, fragmentation profile and elution time—indicates that the impurity at RRT 0.30 is the result of a reaction between the SYN120 and lactose monohydrate in the tablet formulation.

Example 4: Diluent Compatibility Studies with Mannitol

Due to the unexpected compatibility issues of lactose with SYN120, a study for a new diluent for the tablet formulation was performed. Developmental trials were thus conducted using mannitol and microcrystalline cellulose as alternative diluents. The suitability of the diluents was assessed by manufacturing SYN120 100 mg and SYN120 5 mg tablets.

Mannitol is recognized as an inert diluent and as a replacement for lactose, therefore an attempt was made to use this diluent in the manufacture of SYN120 100 mg tablets and SYN120 5 mg tablets. The formulation composition of SYN120 100 mg uncoated tablets using mannitol as a diluent is provided in Table 3 below.

TABLE 3

Tablet Formulation of SYN120 100 mg tablets (mannitol)

| Ingredient | % w/w | mg/tablet | grams/batch |
|---|---|---|---|
| SYN120 | 60 | 100 | 240 |
| Mannitol (Peritol 160C) | 3.6 | 6 | 14.4 |
| Starch 1500 | 25 | 41.67 | 100 |
| Sodium starch glycolate | 5 | 8.33 | 20 |
| Povidone K30 | 5 | 8.33 | 20 |
| Sodium lauryl sulfate | 0.4 | 0.67 | 1.6 |
| Magnesium Stearate | 1 | 1.67 | 4 |
| TOTAL | 100 | 166.67 | 400 |

The formulation was granulated according to Example 1 above (60% w/w granules) by replacing lactose (Pharmatose 350M) with mannitol (Perlitol 160C). In addition the granules were passed through a U3 Comil at 2200 rpm equipped with a 910 micron screen. The granules were dried in a Stea-1 fluid bed drier for 45 minutes at 50° C. The dried granules were lubricated using magnesium stearate by blending for 2 minutes at 25 rpm. The granules were compressed into tablets using the IMA Kilian Pressima equipped with 7 mm tooling; the compression was conducted according to parameters provided below in Table 4.

TABLE 4

Tablet Compression data for SYN120 100 mg tablets (mannitol)

| Compaction force (kN) | 2.7 | 4.5 | 7.2 |
|---|---|---|---|
| Mean tablet hardness (kP) | 3.62 | 6.78 | 7.15 |
| Mean tablet thickness (mm) | 4.42 | 4.15 | 4.02 |
| Mean tablet weight (mg) | 167.4 | 167.3 | 167.1 |
| Friability | complies | complies | complies |

SYN120 5 mg tablets using mannitol were also manufactured. The formulation composition of SYN120 5 mg uncoated tablets using mannitol as a diluent is shown in table 5 below.

TABLE 5

Formulation composition of SYN120 5 mg Tablets (mannitol)

| Ingredient | % w/w | mg/tablet | grams/batch |
|---|---|---|---|
| INTRA-GRANULAR | | | |
| SYN120 | 3.0 | 5 | 24 |
| Mannitol (Peritol 160C) | 0.18 | 0.3 | 1.44 |
| Starch 1500 | 1.25 | 2.08 | 10 |
| Sodium starch glycolate | 0.25 | 0.42 | 2 |
| Povidone K30 | 0.25 | 0.42 | 2 |
| Sodium lauryl sulfate | 0.02 | 0.03 | 0.16 |
| EXTRA-GRANULAR | | | |
| Mannitol (Perlitol 400DC) | 79.00 | 131.67 | 632 |
| Starch 1500 | 10 | 16.67 | 80 |
| Sodium starch glycolate | 5 | 8.33 | 40 |
| Magnesium Stearate | 1.05 | 1.75 | 8.4 |
| TOTAL | 100 | 166.67 | 800.00 |

The final compression blend was manufactured according to the manufacturing process mentioned under Example 2. Lactose (Super Tab 11 SD) was replaced by mannitol (Perlitol 400DC). Note: the 400DC grade was used extra-granularly as the larger particle size is designed to improve flow properties. The blend was compressed into tablets using an IMA Kilian Pressima equipped with 7 mm round tooling. The tablet compression data is shown in Table 6 below.

TABLE 6

Tablet Compression data for SYN120 5 mg tablets (mannitol)

| | |
|---|---|
| Compaction force (kN) | 7.2 |
| Mean tablet hardness (kP) | 1.48 |
| Mean tablet thickness (mm) | 3.96 |
| Mean tablet weight (mg) | 167.1 |
| Friability (% loss) | 6.9 |

As observed from the data, the blend failed to compress, resulting in tablets with a low hardness which would fail friability. Indeed, the mean tablet harness was 1.48 kP at a compaction force of 7.2 kN, and the % loss of friability of 6.9. This data suggests that the use of mannitol (likely in combination with SYN120) as a lubricant contributed to the failure to compress into a tablet. This was unexpected as 100 mg tablets containing mannitol gave acceptable compression results.

Example 5: Diluent Compatibility Studies with Microcrystalline Cellulose

Studies using microcrystalline cellulose as a diluent were also performed. The formulation composition of SYN120 100 mg uncoated tablets using microcrystalline cellulose (MCC) as a diluent is shown in Table 7 below.

TABLE 7

Tablet Formulation of SYN120 100 mg tablets (microcrystalline cellulose)

| Ingredient | % w/w | mg/tablet | grams/batch |
|---|---|---|---|
| SYN120 | 60 | 100 | 240 |
| Microcrystalline cellulose (Avicel PH-101) | 3.6 | 6 | 14.4 |
| Starch 1500 | 25 | 41.67 | 100 |
| Sodium starch glycolate | 5 | 8.33 | 20 |
| Povidone K30 | 5 | 8.33 | 20 |

TABLE 7-continued

Tablet Formulation of SYN120 100 mg tablets (microcrystalline cellulose)

| Ingredient | % w/w | mg/tablet | grams/batch |
|---|---|---|---|
| Sodium lauryl sulfate | 0.4 | 0.67 | 1.6 |
| Magnesium Stearate | 1 | 1.67 | 4 |
| TOTAL | 100 | 166.67 | 400 |

The formulation was granulated according to Example 1 above by replacing lactose (Pharmatose 350M) with MCC (Avicel PH-101). In addition the granules were passed through a U3 Comil equipped with a 910 micron screen.

The granules were dried in a Stea-1 fluid bed drier for 45 minutes at 50° C. The dried granules were lubricated using magnesium stearate. The blend was mixed for 2 minutes at 25 rpm. The granules were then compressed into tablets using an IMA Kilian Pressima equipped with 7 mm tooling; the compression was conducted according parameters mentioned in Table 8.

TABLE 8

Tablet Compression data for SYN120 100 mg tablets (microcrystalline cellulose)

| | | | |
|---|---|---|---|
| Compaction force (kN) | 2.5 | 4.2 | 7.4 |
| Mean tablet hardness (kP) | 3.97 | 7.14 | 7.75 |
| Mean tablet thickness (mm) | 4.33 | 4.10 | 3.96 |
| Mean tablet weight (mg) | 167.2 | 167.0 | 166.8 |
| Friability (% loss) | N/A | 0.3 | N/A |

Example 6: Manufacture of SYN120 5 mg Tablets with Microcrystalline Cellulose

The formulation composition of SYN120 5 mg uncoated tablets using microcrystalline cellulose as a diluent is tabulated in Table 9 below.

TABLE 9

Formulation composition of SYN120 5 mg Tablets (microcrystalline cellulose)

| Ingredient | % w/w | mg/tablet | grams/batch |
|---|---|---|---|
| INTRA-GRANULAR | | | |
| SYN120 | 3.0 | 5 | 24 |
| Microcrystalline cellulose (Avicel PH-101) | 0.18 | 0.3 | 1.44 |
| Starch 1500 | 1.26 | 2.10 | 10.08 |
| Sodium starch glycolate | 0.25 | 0.42 | 2 |
| Povidone K30 | 0.25 | 0.42 | 2 |
| Sodium lauryl sulfate | 0.02 | 0.03 | 0.16 |
| EXTRA-GRANULAR | | | |
| Microcrystalline cellulose (Avicel PH-102) | 64.03 | 106.72 | 512.25 |
| Starch 1500 | 25.01 | 41.68 | 200.07 |
| Sodium starch glycolate | 5 | 8.33 | 40 |
| Magnesium Stearate | 1 | 1.67 | 8 |
| TOTAL | 100 | 166.67 | 800.00 |

The final compression blend was manufactured according to the manufacturing process mentioned in Example 2. Lactose (Super Tab 11SD) was replaced in the extragranular phase by MCC (Avicel PH-102). The blend was compressed into tablets using an IMA Kilian Pressima equipped with 7 mm round tooling.

The tablet compression data is provided in Table 10 below. There were no processing issues encountered during the tablet compression.

TABLE 10

Tablet Compression data for SYN120 5 mg tablets (microcrystalline cellulose)

| | |
|---|---|
| Compaction force (kN) | 2.5 |
| Mean tablet hardness (kP) | 6.32 |
| Mean tablet thickness (mm) | 4.05 |
| Mean tablet weight (mg) | 167.3 |
| Friability (% loss) | 0.4 |

As indicated above, SYN120 5 mg tablets unexpectedly failed to compress into tablets using mannitol as a diluent. Specifically, at a compaction force of 7.2 kN, the mean tablet hardness was only 1.48 kP. The SYN120 5 mg tablets with mannitol also failed friability assessment. In contrast, SYN120 5 mg tablets and 100 mg tablets with microcrystalline cellulose as the diluent had considerably higher mean tablet hardness, even at lower compaction forces, and were found to be acceptable for further development and scale up for clinical supply manufacturing.

Example 7: Scale Up Manufacture of SYN120 Tablets with Microcrystalline Cellulose The manufacture of granules was performed at a scale of 4.8 kg. Table 11 details the formulation composition of the granulation batch (excluding the water that is added during processing). The granules were manufactured using the Diosna VAC-20 high shear granulator and the granules were subsequently dried using the GEA MP1 fluid bed drier. The equipment train used for the manufacture of SYN120 granules is shown in FIG. 5.

TABLE 11

Formulation Composition for SYN120 Granulation Batch

| Ingredient | % w/w | grams/batch |
|---|---|---|
| SYN120 | 60.61 | 2909.1 |
| Microcrystalline cellulose (Avicel PH-101) | 3.64 | 174.6 |
| Starch 1500 | 25.25 | 1212.1 |
| Sodium starch glycolate | 5.05 | 242.4 |
| Povidone K30 | 5.05 | 242.4 |
| Sodium lauryl sulfate | 0.40 | 19.4 |
| TOTAL | 100 | 4800 |

The SYN120 Granulation Batch formulation was designed for multiple uses: (1) it can be blended only with magnesium stearate to produce 100 mg tablets, or (2) it can be blended with additional extra-granular excipients, plus magnesium stearate, to produce tablets of lower strength (for example, 5 mg, 10 mg, or 50 mg tablets).

The following procedure was followed for the manufacture of SYN120 granules. Initially a granulation solution of povidone K-30 was prepared by dissolving the required amount of povidone K-30 into 1483 grams of water, followed by the addition of the required quantity of sodium lauryl sulfate. The solution was continuously stirred for 1 hour using an overhead stirrer. The required quantity of SYN120, microcrystalline cellulose, starch 1500 and sodium starch glycolate were dispensed and screened through a 610 micron hand screen. The screened API and excipients were transferred into the Diosna VAC-20 20 L bowl. The contents of the high shear granulator were then dry mixed.

The contents of the granulator were granulated by adding the granulation solution at a rate of 280 grams/minute. After spraying approximately half of the quantity of the granulating solution, the granulator was stopped to visually inspect the quality of the granules (to ensure over-granulation had not occurred). The granulation process was restarted and was continued until the entire amount of granulating solution was added.

After spraying the entire quantity of granulating fluid it was observed that contents of the granulator were slightly under-granulated and therefore an additional 125 grams of water was added (via spraying). Following the addition of the extra water, the contents of the granulator were mixed for a further 3 minutes (wet massing).

A visual inspection of the granules was performed and it was noticed that the granules had a small particle size with negligible amounts of agglomerates. As a result wet-screening of the granules was considered not necessary (could potentially damage the granules) and was not performed. The granules were then transferred into a GEA MP1 fluid bed drier equipped with a 16 L bowl for drying.

The drying process was performed for approximately 50 minutes. During the drying period, samples of the granules were removed and the loss on drying (LOD) determined. After 50 minutes, an LOD result of 2.3% w/w was reported (target LOD <3%).

Upon unloading the granules from the fluid bed drier, a few agglomerates were observed in the granules. As agglomerates could have the potential to cause uniformity issues in the downstream blending steps (SYN120 50 mg and SYN120 10 mg blend), the granules were passed through a U3 Comil (2500 rpm) equipped with a round impeller and 1395 micron screen. (Note: the Comil is used to de-agglomerate powders and not as a particle size reduction technique.) The yield of the granules after comilling was determined as 92.48% (4439 grams).

The formulation composition of SYN120 50 mg uncoated tablets is detailed in Table 12.

TABLE 12

Tablet Formulation of SYN120 50 mg tablets (microcrystalline cellulose)

| Ingredient | % w/w | mg/tablet | grams/batch |
|---|---|---|---|
| INTRA-GRANULAR | | | |
| SYN120 (Active) | 30.0 | 50.0 | 300 |
| Microcrystalline cellulose (Avicel PH-101) (Diluent) | 1.8 | 3.0 | 18 |
| Starch 1500 (Diluent) | 12.5 | 20.83 | 125 |
| Sodium starch glycolate (Disintegrant) | 2.5 | 4.17 | 25 |
| Povidone K30 (Binder) | 2.5 | 4.17 | 25 |
| Sodium lauryl sulphate (Surfactant) | 0.2 | 0.33 | 2 |
| EXTRA-GRANULAR | | | |
| Microcrystalline cellulose (Avicel PH-102) (Diluent) | 32.0 | 53.34 | 320 |
| Starch 1500 (Diluent) | 12.5 | 20.83 | 125 |
| Sodium starch glycolate (Disintegrant) | 5.0 | 8.33 | 50 |
| Magnesium Stearate (Lubricant) | 1 | 1.67 | 10 |
| TOTAL | 100 | 166.67 | 1000 |

Initially 495 g of SYN120 granules (from 4.8 kg batch above), 50 g of sodium starch glycolate and 320 g of microcrystalline cellulose PH-102 were transferred into a 2 L IBC. The contents of the blender were blended for 5 minutes at 25 rpm.

125 g of starch 1500 was added to the IBC and the contents blended for 10 minutes at 25 rpm. 10 g of magnesium stearate was passed through a 500 micron screen, added to the IBC, and lubricated for 3 minutes at 25 rpm.

The blend was then unloaded into double polyethylene bags

The blend was then compressed using a IMA Pressima rotary tablet press.

The compression data for the SYN120 50 mg formulation is detailed in Table 13.

TABLE 13

Tablet Compression data for SYN120 50 mg tablets

| | |
|---|---|
| Compaction force (kN) | 2.5 |
| Mean tablet hardness (kP) | 9.7 |
| Mean tablet thickness (mm) | 4.07 |
| Mean tablet weight (mg) | 166.5 |
| Friability (% loss) | 0.1 |

A suspension of Opadry yellow was prepared by mixing 0.108 Kg of Opadry into 0.612 Kg of water to give a 14% w/w suspension. The suspension was maintained under continuous stirring.

The tablets were loaded into the O'Hara Labcoat coater equipped with a 12-inch coating pan. The tablets were pre-warmed for 10 minutes, an average weight of 100 pre-warmed tablets was determined and based on this average the target tablet weight was calculated. The average weight of 100 pre-warmed tablets was 166.03 mg and the target weight of coated tablet was 170.00 mg.

During the coating operation 10 tablets were weighed every 10 minutes. The tablets were coated to a weight gain of 2.4%. The average weight of coated tablet was 171.11 mg.

After the target weight was attained, the tablets were dried in the same coating pan for 10 minutes, followed by cooling for 15 minutes. The tablets were then unloaded into double polyethylene bags.

A similar scale up was performed with 100 mg and 10 mg tablet formulations. SYN120 100 mg, 50 mg and 10 mg tablets formulations were successfully scaled-up and no issues occurred during the manufacturing operation. A granulation process was developed which produced acceptable granules (good flow properties and gave acceptable blends when extra-granular materials were added). The manufacturing operation for the final compression blends was felt to be acceptable as all the blends readily passed the blend uniformity criteria (90.0-100.0% LC). In addition all the blends had acceptable flow properties indicating that the blends are suitable for downstream processing.

The tablet compression operation for all the strengths was also performed without any issues. All strengths of core tablets showed good weight control during processing, acceptable friability (all less than or equal to 0.2%) and acceptable disintegration (less than 12 minutes) with an increase in compression force resulting in only a minor increase in disintegration time.

The manufacturing processes for the 10 mg, 50 mg and 100 mg tablets in this example are considered suitable for GMP manufacture.

Example 8: Pharmacokinetic Analysis of SYN120 Tablets (Single Dose)

Pharmacokinetic (PK) analysis was performed on 42 subjects (36 males; 6 females) who received SYN120 oral tablets. In this study, subjects received a single oral dose of SYN120 at one of the following doses: 2 mg; 10 mg; 30 mg; 100 mg; 300 mg; and 600 mg. The SYN120 oral tablets used in this study were formulated for immediate release at tablet strengths of 2 mg, 10 mg, and 50 mg. The tablets were formulated using lactose monohydrate, corn starch, sodium starch glycolate, povidone, sodium lauryl sulfate, magnesium stearate, and the coating agent Opadry Yellow. Blood samples were collected at predose and 0.5, 1, 1.5, 2, 3, 4, 6, 8, 12, 16, 24, 32, 36, 48, and 72 hours postdose. During the treatments at 100 mg and higher, the protocol was amended to include an additional blood sample on Study Day 7 (nominal time of 151 hours). Following oral administration, SYN120 absorption was rapid and plasma levels were measurable in all subjects at the first time point (0.5 hours).

Table 14 below provides a summary of the mean PK parameters of plasma SYN120 for all doses. Mean plasma SYN120 concentrations following single ascending oral doses of 2 to 600 mg SYN120 are also presented in FIG. 6A and FIG. 6B.

Following the attainment of $C_{max}$, SYN120 concentrations declined in a multi-phasic manner. The time of the last measurable concentration ($T_{last}$) increased as dose increased. SYN120 was measurable after up to 72 hours in 1 subject each following 2 and 10 mg, and in most subjects in the 30 mg group. Following the addition of a 7 day time point, SYN120 was measurable in a few subjects.

TABLE 14

Summary of the Mean Pharmacokinetic Parameters of Plasma SYN120 for All Active Treatments

| | Cohort | | | | | | |
|---|---|---|---|---|---|---|---|
| | A | B | C | D | E | F | G |
| SYN120 Dose (mg) | 2 | 10 | 30 | 100 (males) | 100 (females) | 300 | 600 |
| | | | Median (min, max) | | | | |
| $T_{max}$ (hr) | 2.02 (1.00, 4.03) | 1.76 (1.01, 3.00) | 2.26 (1.01, 4.02) | 4.00 (0.501, 6.01) | 2.51 (1.51, 4.02) | 3.53 (3.00, 4.00) | 4.51 (1.00, 6.14) |
| | | | Geometric mean (% CV) | | | | |
| $C_{max}$ (ng/mL) | 11.8 (42.7) | 48.7 (36.0) | 179 (40.6) | 604 (27.3) | 498 (41.3) | 1730 (38.6) | 2080 (38.2) |
| $AUC_{0-t}$ (ng·hr/mL) | 139 (116) | 384 (60.2) | 1753 (62.6) | 7011 (58.0) | 5102 (67.2) | 27380 (41.6) | 42530 (59.6) |
| $AUC_{0-24}$ (ng·hr/mL) | 118 (86.6) | 351 (56.7) | 1542 (56.6) | 5867 (50.2) | 3997 (65.5) | 21310 (44.8) | 27620 (46.1) |
| $AUC_{0-inf}$ (ng·hr/mL) | 146 (117) | 389 (59.2) | 1766 (61.9) | 7065 (58.8) | 5124 (67.0) | 27430 (41.5) | 42920 (59.3) |

TABLE 14-continued

Summary of the Mean Pharmacokinetic Parameters of Plasma SYN120 for All Active Treatments

| | Cohort | | | | | | |
|---|---|---|---|---|---|---|---|
| | A | B | C | D | E | F | G |
| | Artithmetic mean (±SD) | | | | | | |
| $t_{1/2}$ (hr) | 11.4 ± 5.11 | 8.45 ± 2.31 | 8.92 ± 1.39 | 11.0 ± 4.76 | 12.4 ± 8.77 | 9.58 ± 3.46 | 12.0 ± 4.81 |
| CL/F (L/hr) | 18.8 ± 15.2 | 29.0 ± 15.0 | 19.2 ± 9.58 | 15.8 ± 7.56 | 22.5 ± 11.9 | 11.7 ± 4.81 | 15.7 ± 7.98 |
| $V_2$/F (L) | 264 ± 191 | 379 ± 283 | 253 ± 149 | 227 ± 94.2 | 448 ± 500 | 154 ± 57.3 | 246 ± 97.6 |

N = 6 active and 2 placebo/group. Pharmacokinetic parameters were calculated only for subjects in the active treatment groups. BLQ plasma samples (samples below the lower limit of quantitation) were treated as '0.00' before the first quantifiable concentration and as 'missing' elsewhere.

Overall, mean peak plasma concentrations were reached approximately 2 to 4.5 hours after single doses of 2 to 600 mg SYN120. On average, peak plasma SYN120 concentrations were attained at a $T_{max}$ of approximately 2 hours after dosing from 2 to 30 mg SYN120. Median $T_{max}$ tended to be longer at doses of 100 mg and above, based on $T_{max}$ estimates of approximately 4 hours in the higher dose groups.

Mean $C_{max}$ and mean AUC increased as dose increased, and percent extrapolated for $AUC_{0-inf}$ from $AUC_{0-t}$ was minimal. The mean apparent SYN120 elimination half-life was generally comparable across treatment groups and ranged between 8.45 and 12.4 hours. Similarly, there was no consistent trend indicating clear differences in either clearance or volume of distribution with increasing doses of SYN120.

The observed intersubject variability in SYN120 PK parameters was large and not dose-related, with individual PK parameter data generally overlapping between cohorts. The geometric CV for the extent of exposure ranged between 41.5 and 67.2% for $AUC_{0-t}$, $AUC_{0-24}$ and $AUC_{0-inf}$ estimates, except at the lowest dose where the CV ranged between 86.6 and 117%. The variability of all other PK parameters was similarly large.

There was also a noticeable difference between females and males at the 100 mg group. Specifically, the mean peak and systemic exposure of SYN120 was consistently greater in males compared to females following a single dose of SYN120 100 mg. Mean estimates of $C_{max}$, $AUC_{0-t}$, $AUC_{0-24}$ and $AUC_{0-inf}$ were approximately 1.2- to 1.5-fold greater and the median $T_{max}$ tended to occur later in males (4.00 hours) compared to females (2.51 hours). Assuming the fraction of SYN120 absorbed was similar between genders, the difference in exposure was consistent with a greater clearance and volume of distribution in females with values of 22.5 L/h and 448 L, respectively, versus 15.8 L/h and 227 L, respectively, in males. Consequently, mean estimates of $t_{1/2}$ were comparable between genders (11.0 and 12.4 hours). Table 15 below shows the PK parameters between males and females at 100 mg as a single dose.

TABLE 15

Pharmacokinetic Parameters of SYN120 in males and females following 100 mg of SYN120 in a single dose

| | Males | Females | p-value* |
|---|---|---|---|
| $C_{max}$ (ng/mL) | 623 ± 180 | 532 ± 218 | 0.347 |
| $AUC_{0-t}$ (ng · h/mL) | 7979 ± 4805 | 5963 ± 3651 | 0.361 |
| $AUC_{0-24}$ (ng · h/mL) | 6473 ± 3333 | 4672 ± 2993 | 0.246 |
| $AUC_{0-inf}$ (ng · h/mL) | 8061 ± 4881 | 5984 ± 3661 | 0.358 |

*t-test performed using the geometric means, table contains arithmetic mean

Although the mean $C_{max}$ and AUC values appeared to be greater in males compared to females, t-test showed that there was no statistically significant difference in the PK parameters ($C_{max}$ and AUC values) between males and females, possibly as a result of the small sample size and high intersubject variability in the PK parameters.

Example 9: Pharmacokinetic Analysis of SYN120 Tablets (Multiple Dose)

PK analysis in a multiple dose study was performed on 28 subjects (10 males and 18 females) on day 1 and on 27 subjects (10 males and 17 females) on day 14 who received SYN120 oral tablets. The dosing interval was once daily, approximately 40 minutes after a standard breakfast, for up to 21 days. The subjects were administered the same dose of SYN120 daily at one of the following doses: 100 mg; 300 mg; and 600 mg. The SYN120 oral tablets used in this study were the 50 mg tablets as described in Example 8.

Plasma samples were prepared from blood samples for PK analysis collected on days 1 and 14 at the following time points: 0, 0.5, 1, 1.5, 2, 3, 4, 6, 8, 12, and 24 hrs postdose. Additional blood samples were taken following administration on Day 14 at 32, 36, 48, 72, and 168 hrs (day 15 through day 21). In addition, on days 4 and 10, predose blood samples were collected, while on day 7, blood samples were collected predose and 4 hrs postdose. Table 16 below shows PK statistics at Day 1 and Day 14. Mean plasma SYN120 concentrations at Day 1, (FIG. 7A and FIG. 7B), and at Day 14 (FIG. 8A and FIG. 8B) are also provided.

TABLE 16

Summary of Mean PK Parameters Statistics of Plasma SYN120 at Day 1 and Day 14

| | Day 1 | | | Day 14 | | |
|---|---|---|---|---|---|---|
| | 100 mg QD[a] | 300 mg QD[b] | 600 mg QD[a] | 100 mg QD[a] | 300 mg QD[b] | 600 mg QD[c,d] |
| Geometric Mean (% CV) | | | | | | |
| $AUC_{0-24}$ (ng-h/mL) | 7783 (57.3) | 29505 (45.0) | 59589 (56.5) | 14175 (32.6) | 36021 (20.9) | 56076 (23.6) |
| $AUC_{0-last}$ (ng-h/mL) | 7779 (57.3) | 29491 (45.0) | 59563 (56.5) | 19233 (39.2) | 45749 (34.7) | 74048 (40.7) |
| $C_{max}$ (ng/mL) | 813 (37.1) | 2747 (34.1) | 5176 (36.9) | 1244 (20.7) | 3468 (25.4) | 5465 (19.0) |

TABLE 16-continued

Summary of Mean PK Parameters Statistics of Plasma SYN120 at Day 1 and Day 14

|  | Day 1 | | | Day 14 | | |
| --- | --- | --- | --- | --- | --- | --- |
|  | 100 mg QD$^a$ | 300 mg QD$^b$ | 600 mg QD$^a$ | 100 mg QD$^a$ | 300 mg QD$^b$ | 600 mg QD$^{c,d}$ |
| $C_{ss}$ (ng/mL) | — | — | — | 591 (32.6) | 1501 (20.9) | 2336 (23.6) |
| $C_{min}$ (ng/mL) | — | — | — | 201 (56.7) | 357 (42.7) | 520 (64.2) |
| Arithmetic Mean (% CV) | | | | | | |
| Half-Life (h) | — | — | — | 15.4 (11.8) | 15.5 (55.5) | 15.0 (21.1)$^e$ |
| % Fluctuation | — | — | — | 177 (20.0) | 209 (19.8) | 212 (18.0) |
| $C_{max}$ AR | — | — | — | 1.55 (17.2) | 1.30 (27.6) | 1.14 (35.0) |
| $AUC_{0-24}$ AR | — | — | — | 1.87 (23.1) | 1.29 (34.0) | 1.05 (44.8) |
| Ae % | 0.610 (35.5)$^f$ | 0.857 (43.6) | 0.997 (56.7) | 1.15 (32.9) | 0.988 (29.0) | 0.756 (35.1) |
| 0-24 Clr (mL/min) | 1.25 (21.8) | 1.33 (23.8) | 1.45 (20.9) | 1.33 (23.4) | 1.34 (16.2) | 1.31 (19.7) |
| Median (Min, Max) | | | | | | |
| $T_{max}$ | 4.00 (1.43, 6.00) | 4.00 (2.00, 6.00) | 4.00 (3.00, 6.00) | 3.00 (2.00, 4.00) | 3.00 (1.43, 4.00) | 3.51 (2.00, 4.00) |
| $T_{last}$ | — | — | — | 168 (72-168) | 168 (72-168) | 168 (168-168) |

The PK of SYN120 showed large intersubject variability following administration of a single oral dose of 100, 300, or 600 mg SYN120, which is consistent with the Single dose portion of this study (Example 8). On Study Day 1, mean peak plasma concentrations between 813 and 5176 ng/mL were reached at a median $T_{max}$ of 4 hrs in each dose group. $AUC_{0-24}$ values averaged 7783, 29505, and 59589 ng-h/mL, respectively, for the 3 dose groups. Day 14 mean peak plasma concentrations of 1244, 3468, and 5465 ng/mL were reached at a median $T_{max}$ between 3.00 and 3.51 hrs. $AUC_{0-24}$ averaged 14175, 36021, and 56076 ng-h/mL, respectively, over the dose range studied and $AUC_{0-last}$ averaged 19233, 45749, and 74048 ng-h/mL, respectively. The intersubject variability in $C_{max}$ and AUC values on Day 14 was considerably decreased compared to Day 1 (19.0% to 40.7% versus 34.1% to 57.3%).

Example 10: Pharmacokinetic Analysis of SYN120 Tablets Administered at a Dose of 100 mg SYN120 QD Patients taking SYN120 are titrated from a starting dose of 20 mg SYN120 QD for the first 7 days, followed by 50 mg SYN120 QD for the next 7 days, then 100 mg SYN120 QD for the remaining portion of the study. Plasma samples are taken on study weeks 4, 8 and 16, and a shown below in Table 17.

TABLE 17

Summary of Plasma Concentrations of SYN120
Concentration ng/mL

| | Time range/h | | | | |
| --- | --- | --- | --- | --- | --- |
| | 0.5 h-1.5 h | 1.5 h-2.5 h | 2.5 h-3.5 h | 3.5 h-4.5 h | 4.5 h-7.5 h |
| | 8.57 | 430 | 1620 | 1190 | 1210 |
| | 309 | 581 | 767 | 1470 | 850 |
| | 1310 | 120 | 1660 | 1330 | 1160 |
| | 297 | 558 | 355 | 855 | 124 |
| | 116 | 314 | 473 | 24.2 | 344 |
| | 476 | 705 | 410 | 467 | 989 |
| | 326 | 229 | 1220 | | |
| | | 235 | | | |
| n | 7 | 8 | 7 | 6 | 6 |
| Mean | 406.1 | 396.5 | 929.3 | 889.4 | 779.5 |
| Sd | 426.6 | 204.9 | 567.1 | 556.7 | 446.8 |

TABLE 17-continued

Summary of Plasma Concentrations of SYN120
Concentration ng/mL

| | Time range/h | | | | |
| --- | --- | --- | --- | --- | --- |
| | 0.5 h-1.5 h | 1.5 h-2.5 h | 2.5 h-3.5 h | 3.5 h-4.5 h | 4.5 h-7.5 h |
| Min | 8.57 | 120 | 355 | 24.2 | 124 |
| Median | 309 | 372 | 767 | 1023 | 920 |
| Max | 1310 | 705 | 1660 | 1470 | 1210 |

The results show that the administration of compositions of the present invention at 100 mg SYN120 QD provide median steady state plasma levels ($C_{SS}$) between about 300 ng/mL to about 1100 ng/mL.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A tablet comprising a therapeutically effective amount of SYN120 or a pharmaceutically acceptable salt thereof, wherein the tablet is substantially free of lactose.

2. The tablet of claim 1, wherein said tablet is substantially free of isomers of lactose selected from the group consisting of sucrose, trehalose, maltose, isomaltose, maltulose, isomaltulose, turanose, and cellobiose.

3. The tablet of claim 1, wherein said tablet is substantially free of all isomers of lactose.

4. The tablet of claim 3, wherein said tablet is substantially free of reducing sugars selected from the group consisting of galactose, glucose, fructose, ribose, xylose, and isomers thereof.

5. The tablet of claim 4, wherein said tablet is substantially free of any reducing sugar or an isomer thereof.

6. The tablet of claim 1, wherein said tablet comprises about 2.5 mg to about 200 mg of SYN120 or a pharmaceutically acceptable salt thereof.

7. The tablet of claim 1, wherein said tablet comprises about 50 mg to about 100 mg of SYN120 or a pharmaceutically acceptable salt thereof.

8. The tablet of claim 1, wherein said tablet comprises about 5 mg to about 15 mg of SYN120 or a pharmaceutically acceptable salt thereof.

9. The tablet of claim 1, wherein said tablet is an immediate release tablet.

10. The tablet of claim 1, wherein at least about 90% of said SYN120 or a pharmaceutically acceptable salt thereof is released in 60 minutes when tested for dissolution using a USP II paddle apparatus at a speed of 75 rpm in 900 mL of 0.2% w/v Sodium Lauryl Sulfate (SLS) in pH 1.2 Hydrochloric Acid (37% v/v) at 37° C.

11. The tablet of claim 1, wherein at least about 80% of said SYN120 or a pharmaceutically acceptable salt thereof is released in 30 minutes when tested for dissolution using a USP II paddle apparatus at a speed of 75 rpm in 900 mL of 0.2% w/v Sodium Lauryl Sulfate (SLS) in pH 1.2 Hydrochloric Acid (37% v/v) at 37° C.

12. The tablet of claim 1, wherein at least about 70% of said SYN120 or a pharmaceutically acceptable salt thereof is released in 15 minutes when tested for dissolution using a USP II paddle apparatus at a speed of 75 rpm in 900 mL of 0.2% w/v Sodium Lauryl Sulfate (SLS) in pH 1.2 Hydrochloric Acid (37% v/v) at 37° C.

13. The tablet of claim 1, wherein said tablet is substantially free of mannitol.

14. The tablet of claim 1, wherein said tablet is substantially free of all isomers of mannitol.

15. The tablet of claim 1, wherein said tablet is substantially free of the compounds selected from the group consisting of sorbitol, xylitol, erythritol, lactitol, and maltitol.

16. The tablet of claim 1, wherein said tablet has a mean tablet hardness of about 4 kP to about 15 kP.

17. The tablet of claim 1, wherein said tablet additionally comprises microcrystalline cellulose.

18. The tablet of claim 17, wherein said microcrystalline cellulose is a microcrystalline cellulose prepared by partial depolymerization of alpha-cellulose having a nominal particle size of about 20 μm to about 180 μm.

19. The tablet of claim 1, wherein after the administration of a single tablet to a patient, the tablet provides a SYN120 $T_{max}$ ranging from about 1 hr to about 4 hrs.

20. The tablet of claim 1, wherein after the administration of a single tablet to a patient, the tablet provides a SYN120 mean $T_{max}$ ranging from about 1.5 hrs to about 5 hours.

21. The tablet of claim 1, wherein after the administration of a single tablet to a patient, the tablet provides a SYN120 mean $C_{max}$ ranging from about 4 ng/mL to 6.5 ng/mL per mg dosed.

22. The tablet of claim 1, wherein after administration of a single tablet to a patient, the tablet provides a SYN120 mean $AUC_{0-24}$ ranging from about 100 ng-hr/mL to about 6,000 ng-hr/mL.

23. The tablet of claim 1, wherein after administration of a single tablet to a patient, the tablet provides a SYN120 mean $AUC_{0-inf}$ ranging from about 100 ng-hr/mL to about 7,500 ng-hr/mL.

* * * * *